United States Patent [19]

Hirai et al.

[11] Patent Number: 5,028,610

[45] Date of Patent: Jul. 2, 1991

[54] N-BENZHYDRYL-SUBSTITUTED HETEROCYCLIC DERIVATIVES, THEIR PREPARATION AND THEIR USE

[75] Inventors: Koichi Hirai; Yuji Iwano; Katsumi Fujimoto; Yoshiki Matsui, all of Hiromachi, Japan

[73] Assignee: Sankyo Company Limited, Tokyo, Japan

[21] Appl. No.: 167,354

[22] Filed: Mar. 14, 1988

[30] Foreign Application Priority Data

Mar. 18, 1987 [JP] Japan .................................. 62-63157

[51] Int. Cl.$^5$ .................... A61K 31/495; C07D 241/04
[52] U.S. Cl. .................................... 514/259; 540/553; 540/575; 544/238; 544/295; 544/357; 544/370; 544/384; 544/385; 544/396; 544/397
[58] Field of Search ................ 514/255; 544/384, 385, 544/396, 397

[56] References Cited

U.S. PATENT DOCUMENTS

| | | | |
|---|---|---|---|
| 4,591,590 | 5/1986 | Ueda et al. | 544/396 |
| 4,675,319 | 6/1987 | Nardi et al. | 544/396 |
| 4,780,495 | 10/1988 | Lai et al. | 544/397 |
| 4,868,184 | 9/1989 | Toth et al. | 544/397 |

FOREIGN PATENT DOCUMENTS 207901 7/1987 European Pat. Off. ............ 544/396

OTHER PUBLICATIONS

Freifelder, "J.A.C.S.", vol. 82, 1960, pp. 2386-2389.
Wright et al., "Chemical Abstracts", vol. 68, 1968, col. 86028d.
Vadodario et al., "Chemical Abstracts", vol. 71, 1969, col. 101817t.
Ragnier et al. "Chemical Abstracts", vol. 74, 1971, col. 31778s.
Patel et al., "Chemical Abstracts", vol. 75, 1971, col. 31808x.
Regnier, et al. "Chemical Abstracts", vol. 82, 1975, col. 112035q.
Arai et al., "Chemical Abstracts", vol. 103, 1985, col. 103:16527h.
Chiarino et al., "Chemical Abstracts", vol. 103, 1985, col. 103:178033w.
Wakabayashi et al., "Chemical Abstracts", vol. 104, 1986, col. 104:168177c.
Elban et al., "Chemical Abstracts", vol. 109, 1988, col. 109:92792e.
Doe et al., "Chemical Abstracts", vol. 109, 1988, col. 109:90042e.
Sugiura et al., "Chemical Abstracts", vol. 110, 1989, col. 110:23502u.
Hirai et al., "Chemical Abstracts", vol. 110, 1989, col. 110:57692w.
Wakabayashi et al., "Chemical Abstracts", vol. 111, 1989, col. 111:23234d.
Sakane et al., "Chemical Abstracts", vol. 112, 1990, col. 112:7495e.
The Merck Index-10th Edition, 1983, No. 2267, Cinepazide, pp. 325-326.
The Merck Index-10th Edition, 1983, No. 2281, Cinnarizine, pp. 327-328.
The Merck Index-10th Edition, 1983, No. 4045, Flunarizine, p. 592.

Primary Examiner—C. Warren Ivy
Assistant Examiner—James H. Turnipseed
Attorney, Agent, or Firm—Frishauf, Holtz, Goodman & Woodward

[57] ABSTRACT

Compounds of formula (I):

A—M—B—         (I)

(in which: M represents a saturated heterocyclic group having from 5 to 7 ring atoms of which 2 are nitrogen atoms, said group being unsubstituted or being substituted at any of its carbon atoms by $C_1$-$C_6$ alkyl and/or oxo substituents: A represents a halo-substituted benzhydryl substituent; and B represents certain specific substituted alkyl groups) and salts thereof are valuable for the treatment and prophylaxis of disorders arising from circulatory problems, especially those affecting the brain. They may be prepared by reacting a compound of formula A—M—H with a halo or acyloxy derivative corresponding to the alkyl substituent B which it is desired to introduce.

23 Claims, No Drawings

N-BENZHYDRYL-SUBSTITUTED HETEROCYCLIC DERIVATIVES, THEIR PREPARATION AND THEIR USE

BACKGROUND TO THE INVENTION

The present invention relates to a series of novel heterocyclic compounds having a saturated heterocyclic ring containing two ring nitrogen atoms, one of which is substituted by a halobenzhydryl group and the other of which is substituted by specific substituted alkyl groups. The invention also provides a pharmaceutical composition for the treatment, inter alia, of disorders affecting circulation within the brain, and also provides methods of using the compounds and processes for preparing them.

Maintenance of a good blood circulation is absolutely vital to continued good health in humans and other animals, and many compounds, of the class known generally as "vasodilators", have been used or proposed to be used to assist the circulation of the blood and/or to relieve symptoms arising from poor circulation. However, one of the most damaging and distressing consequences of circulatory problems is damage to the brain, which may be non-fatal but irreversible and can have serious effects on the personality and behavior of the patient. Similar problems may also arise from other ischemic events, which may or may not be the consequence of circulatory disorders. Unfortunately, relatively few of the many vasodilators available are indicated for use in the treatment of cerebral vascular insufficiency.

In accordance with the present invention, we have now discovered a series of new compounds which have shown exciting possibilities for the treatment of cerebral vascular disorders. The new compounds of the invention are characterized by a saturated heterocyclic ring containing two ring nitrogen atoms (e.g. an imidazolidine, piperazine or homopiperazine ring), one of the nitrogen atoms having a halobenzhydryl substituent and the other having a substituent comprising an alkyl group, itself having certain specific substituents thereon.

Of the several compounds which have been proposed for use in the treatment and prophylaxis of cerebral vascular disorders, the two compounds which most closely resemble those of the present invention, in terms both of molecular structure and pharmacological effects, are flunarizine (which itself was developed from the closely related drug cinnarizine) and cinepazide. Flunarizine and cinepazide are described in The Merck Index, Tenth Edition, published by Merck & Co. Inc., 1983, in monographs 4045 and 2267 respectively. These compounds are included amongst the compounds covered by United Kingdom Patents No. 1 268 710 and 1 218 591, respectively. Flunarizine has the formula (A) given below, whilst cinepazide has the formula (B):

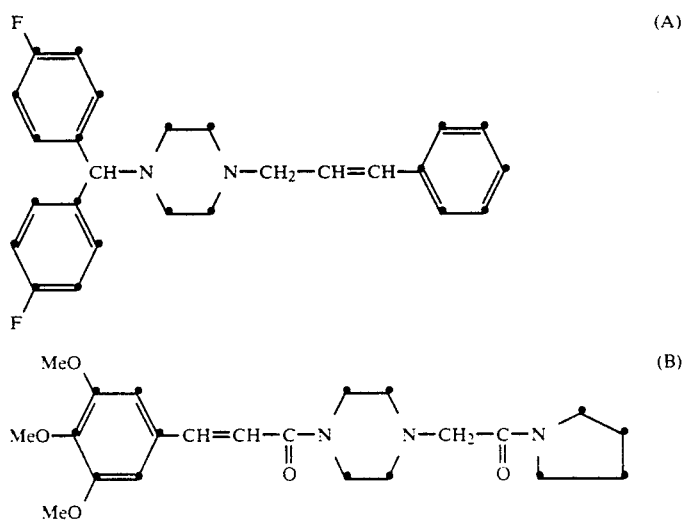

In the above formulae, Me represents the methyl group.

These compounds are known to be calcium-entry blockers, i.e. they block or reduce the entry of calcium (as $Ca^{2+}$) into cells of the animal body. Calcium buildup in vulnerable brain cells has been shown to have a significant correlation with irreversible cell damage, and thus compounds which can reduce the entry of calcium into these cells can be expected to assist in the prevention of such damage. Calcium buildup in cells can be caused by ischemia (i.e. an inadequate supply of oxygen to the organ or part of the body containing the cells), and calcium-entry blockers, such as flunarizine and cinepazide, have been found to give a degree of protection against the deleterious effects of ischemia, even when the drug is administered after the onset of ischemia.

We have now discovered a series of new compounds structurally related to flunarizine, but which have significantly better pharmacological effects. In particular, they improve blood circulation, especially in the brain, are excellent selective calcium-entry and overload blockers and confer a significant degree of protection against morbidity arising from reduced oxygen intake, e.g. as a result of breathing an oxygen-poor atmosphere. Moreover, the compounds of the present invention have shown a significantly lower toxicity than do the prior art compounds.

BRIEF SUMMARY OF INVENTION

It is, accordingly, an object of the present invention to provide, as a new composition of matter, certain new compounds acting as calcium-entry and overload blockers.

It is a further, and more specific, object of the invention to provide such compounds having improved calcium-entry and overload blocking effect and the ability to protect against the adverse effects of anoxia.

It is a still further object of the invention to provide pharmaceutical compositions for the treatment of vascular disorders, especially cerebral vascular disorders, and for protection against the adverse effects of anoxia comprising at least one of the compounds of the invention as the active agent.

It is a still further object of the invention to provide methods for using these compounds and processes for preparing them.

The compounds of the present invention are thus those compounds of formula (I):

A—M—B     (I)

in which:

M represents a saturated heterocyclic group having from 5 to 7 ring atoms of which 2 are nitrogen atoms, said group being unsubstituted or being substituted at any of its carbon atoms by substituents selected from the group consisting of $C_1$-$C_6$ alkyl groups and oxo groups;

A represents a substituent on one of said nitrogen atoms and has the formula (II):

in which $Ar^1$ represents a phenyl group having a substituent $X^1$, and $Ar^2$ represents a phenyl group having a substituent $X^2$, where one of $X^1$ and $X^2$ represents a hydrogen atom or a halogen atom and the other of $X^1$ and $X^2$ represents a halogen atom;

B represents a substituent on the other nitrogen atom and has the formula (III):

in which:

$R^1$ represents a hydrogen atom or a $C_1$-$C_6$ alkyl group;

Y represents a group of formula —$NR^5$—;

$R^4$ and $R^5$ are independently selected from the group consisting of hydrogen atoms, aryl groups, $C_1$-$C_6$ alkyl groups, substituted $C_1$-$C_6$ alkyl groups having at least one substituent selected from the group consisting of substituents (a), $C_3$-$C_{10}$ cycloalkyl groups, aromatic heterocyclic groups and $C_2$-$C_6$ alkenyl groups, or —Y—$R^4$ jointly represents a monocyclic heterocyclic group or a monocyclic heterocyclic group having an aromatic ring fused thereto;

said cycloalkyl groups are unsubstituted or have at least one substituent selected from the group consisting of $C_1$-$C_4$ alkyl groups, and are saturated or have at least one ethylenically unsaturated carbon-carbon double bond;

said aryl groups are carbocyclic aromatic groups having from 6 to 14 ring carbon atoms and are unsubstituted or have at least one substituent selected from the group consisting of substituents (b) and substituents (c);

said aromatic heterocyclic groups have a heterocyclic ring containing from 5 to 7 ring atoms of which from 1 to 3 are hetero-atoms selected from the group consisting of nitrogen, oxygen and sulfur hetero-atoms or have said heterocyclic ring fused to a heterocyclic or carbocyclic ring having from 5 to 7 ring atoms, said aromatic heterocyclic groups being unsubstituted or having at least one substituent selected from the group consisting of substituents (b) and substituents (d);

said monocyclic heterocyclic groups have from 4 to 12 ring atoms of which from 1 to 5 are hetero-atoms selected from the group consisting of nitrogen, oxygen and sulfur hetero-atoms and, where they are fused to an aromatic ring, said aromatic ring is a heterocyclic or carbocyclic ring having from 6 to 12 ring atoms, said monocyclic heterocyclic groups and said aromatic rings being unsubstituted or having at least one substituent selected from the group consisting of substituents (b) and substituents (d);

substituents (a):

halogen atoms, aryl groups, hydroxy groups, $C_1$-$C_6$ alkoxy groups, nitro groups, cyano groups, heterocyclic groups, carboxy groups, $C_2$-$C_7$ alkoxycarbonyl groups, aryloxycarbonyl groups, aralkyloxycarbonyl groups where the alkyl part is $C_1$-$C_4$, $C_1$-$C_7$ aliphatic carboxylic acyl groups, aromatic carboxylic acyl groups and heterocyclic carboxylic acyl groups;

substituents (b):

$C_1$-$C_4$ alkyl groups, nitro groups, cyano groups, hydroxy groups, $C_1$-$C_4$ alkoxy groups, aryloxy groups, aralkyloxy groups where the alkyl part is $C_1$-$C_4$, $C_1$-$C_7$ aliphatic carboxylic acyloxy groups, aromatic carboxylic acyloxy groups, $C_1$-$C_4$ alkylthio groups, arylthio groups, aralkylthio groups where the alkyl part is $C_1$-$C_4$, $C_1$-$C_4$ alkylsulfinyl groups, $C_1$-$C_4$ alkylsulfonyl groups, arylsulfinyl groups, arylsulfonyl groups, $C_1$-$C_7$ aliphatic carboxylic acylamino groups, aromatic carboxylic acylamino groups, $C_2$-$C_7$ alkoxycarbonylamino groups, aralkyloxycarbonylamino groups where the alkyl part is $C_1$-$C_4$, $C_2$-$C_7$ alkoxycarbonyl groups, aryloxycarbonyl groups, aralkyloxycarbonyl groups where the alkyl part is $C_1$-$C_4$, $C_1$-$C_7$ aliphatic carboxylic acyl groups, aromatic carboxylic acyl groups, heterocyclic carboxylic acyl groups, carbamoyl groups, alkylcarbamoyl groups where the alkyl part is $C_1$-$C_4$, dialkylcarbamoyl groups where each alkyl part is $C_1$-$C_4$, thiocarbamoyl groups, alkyl(thiocarbamoyl) groups where the alkyl part is $C_1$-$C_4$, dialkyl(thiocarbamoyl) groups where each alkyl part is $C_1$-$C_4$, ureido groups, alkylureido groups where the alkyl part is $C_1$-$C_4$, dialkylureido groups where each alkyl part is $C_1$-$C_4$, thioureido groups, alkyl(thioureido) groups where the alkyl part is $C_1$-$C_4$, dialkyl(thioureido) groups where each alkyl part is $C_1$-$C_4$, $C_3$-$C_8$ cycloalkyl groups, $C_5$-$C_8$ cycloalkenyl groups, aryl groups, heterocyclic groups, halogen atoms, $C_1$-$C_6$ alkyl groups having at least one halogen substituent, mercapto groups, amino groups, $C_1$-$C_4$ alkylamino groups, dialkylamino groups where each alkyl part is $C_1$-$C_4$, carboxy groups, ($C_1$-$C_4$ hydroxyalkyl)amino groups, di($C_1$-$C_4$ hydroxyalkyl)amino groups, guanidino groups and guanidino groups having at least one $C_1$-$C_4$ alkyl substituent;

PROVIDED THAT, where substituent (a) or (b) represents a group which itself is further substituted by a substituent selected from the group consisting of substituents (a) and (b), that substituent is not further substituted;

substituents (c):

alkylenedioxy groups having from 1 to 6 carbon atoms;

substituents (d):

oxygen atoms;

and pharmaceutically acceptable salts thereof.

The invention further provides a pharmaceutical composition comprising a compound of formula (I) or a pharmaceutically acceptable salt thereof in admixture with a pharmaceutically acceptable carrier or diluent.

The invention still further provides a method for the treatment of vascular disorders, especially cerebral Vascular disorders, in an animal, especially a mammal, e.g. a human being by administering to said animal an effective amount of a compound of formula (I) or a pharmaceutically acceptable salt thereof.

The invention still further provides a method for the treatment of ischemic disorders, especially cerebral ischemic disorders, in an animal, especially a mammal, e.g. a human being, by administering to said animal an effective amount of a compound of formula (I) or a pharmaceutically acceptable salt thereof.

The invention still further provides a method of protecting an animal, especially a mammal, e.g. a human being, against the deleterious effects of anoxia by administering to said animal an effective amount of a compound of formula (I) or a pharmaceutically acceptable salt thereof.

The invention still further provides processes for preparing the compounds of the invention, as described in greater detail hereafter.

DETAILED DESCRIPTION OF INVENTION

In the compounds of the present invention, M represents a saturated heterocyclic group having from 5 to 7 ring atoms of which 2 are nitrogen atoms, the group being substituted or unsubstituted. Examples of suitable such heterocyclic groups include the imidazolidinyl, hexahydropyridazinyl, hexahydropyrimidinyl, piperazinyl, 1,2-diazacycloheptyl, 1,3-diazacycloheptyl and homopiperazinyl groups, of which the saturated heterocyclic groups containing 6 or 7 ring atoms are preferred, the piperazinyl and homopiperazinyl groups being more preferred.

Such heterocyclic groups may be substituted or unsubstituted, and, if substituted, the substituents are selected from the group consisting of oxygen atoms and $C_1-C_6$ alkyl groups, which may be straight or branched chain groups. Examples of alkyl groups included amongst such substituents are the methyl, ethyl, propyl, isopropyl, butyl, isobutyl, sec-butyl, t-butyl, pentyl, isopentyl, 2-methylbutyl, neopentyl, hexyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl and 2,3-dimethylbutyl groups, of which those alkyl groups containing from 1 to 4 carbon atoms are preferred.

There is no criticality as to the number of substituents on the heterocyclic group represented by M, and the only limit on the number of substituents is dictated by the number of substitutable positions and, in some cases, by steric constraints. We prefer those compounds having no more than 2 oxo substituents and/or no more than 4 alkyl substituents.

Where $X^1$ or $X^2$ represents a halogen atom, this may be a fluorine, chlorine, bromine or iodine atom, of which the fluorine and chlorine atoms are preferred. One of $X^1$ and $X^2$ may be a halogen atom and the other may be a hydrogen atom, or both $X^1$ and $X^2$ may be halogen atoms. We especially prefer those compounds in which one of $X^1$ and $X^2$ represents a chlorine atom and the other represents a hydrogen atom or in which both $X^1$ and $X^2$ represent fluorine atoms. Preferably, where $X^1$ and/or $X^2$ represents a halogen atom, this is present on the phenyl group represented by $Ar^1$ and/or $Ar^2$ in the para position.

Where $R^1$ represents an alkyl group, this has from 1 to 6 carbon atoms, and may be a straight or branched chain group. Examples include those listed above as substituents on heterocyclic groups, the $C_1-C_4$ alkyl groups being preferred, and the methyl group being most preferred.

Where $R^4$ or $R^5$ represents an aryl group, this may optionally be substituted with one or more of the substituents listed above as substituents (t) or (c), but preferably: lower alkyl groups; halogen atoms; lower alkoxy groups; or lower alkylenedioxy groups. As with the substituents on heterocyclic groups, there is, in principle, no restriction on the number of such substituents, except those dictated by the number of substitutable positions and steric constraints, but we generally find it convenient if, where the group is substituted, there are from 1 to 3 such substituents. Examples include such unsubstituted aryl groups as the phenyl or naphthyl (1- or 2- naphthyl) groups and corresponding groups which are substituted by one or more of the substituents listed above. For example, examples of groups having at least one alkyl substituent include the 4-methylphenyl, 2-methylphenyl, 3-methylphenyl, 4-ethylphenyl, 4-butylphenyl, 2-propylphenyl, 3-hexylphenyl, 2,3-dimethylphenyl, 3,4-dimethylphenyl, 2,5-dimethylphenyl, 2,6-dimethylphenyl, 2,4-dimethylphenyl, 2,3-diethylphenyl, 3,4-dipropylphenyl, 2,5-dibutylphenyl, 2,6-dipentylphenyl, 2,4-dihexylphenyl, 2,3,6-trimethylphenyl, 2,3,4-trimethylphenyl, 3,4,5-trimethylphenyl, 2,5,6-trimethylphenyl, 2,4,6-trimethylphenyl, 2,3,6-triethylphenyl, 2,3,4-tripropylphenyl, 3,4,5-tributylphenyl, 2,5,6-tripentylphenyl, 2,4,6-trihexylphenyl, 1-methyl-2-naphthyl, 2-methyl-1-naphthyl, 3-methyl-1-naphthyl, 2-ethyl-1-naphthyl, 1-butyl-2-naphthyl, 2-propyl-1-naphthyl, 3-hexyl-1-naphthyl, 2,3-dimethyl-1-naphthyl, 3,8-dimethyl-1-naphthyl, 4,8-dimethyl-1-naphthyl, 5,6-dimethyl -1-naphthyl, 2,4-dimethyl-1-naphthyl, 2,3-diethyl -1-naphthyl, 3,4-dipropyl-1-naphthyl, 4,5-dibutyl -1-naphthyl, 5,6-dipentyl-1-naphthyl, 2,4-dihexyl -1-naphthyl. 2,3,6-trimethyl-1-naphthyl, 2,3,4-trimethyl-1-naphthyl, 3,4,5-trimethyl-1-naphthyl, 4,5,6-trimethyl-1-naphthyl, 2,4,8-trimethyl-1-naphthyl, 2,3,6-triethyl-1-naphthyl, 2,3,4-tripropyl-1-naphthyl, 3,4,8-tributyl-1-naphthyl, 4,5,6-tripentyl-1-naphthyl and 2,4,6-trihexyl-1-naphthyl groups. Examples of aryl groups having at least one halogen substituent include the 4-fluorophenyl, 2-fluorophenyl, 3-fluorophenyl, 4-chlorophenyl, 4-bromophenyl, 2-iodophenyl, 3-chlorophenyl, 3,5-difluorophenyl, 2,5-difluorophenyl, 2,5-diiodophenyl, 2,6-difluorophenyl, 2,4-difluorophenyl, 2,3-dichlorophenyl, 3,4-dichlorophenyl, 2,5-dichlorophenyl, 2,6-dichlorophenyl, 2,4-dibromophenyl, 2,3,6-trifluorophenyl, 2,3,4-trifluorophenyl, 3,4,5-trifluorophenyl, 2,5,6-trifluorophenyl, 2,4,6-trifluorophenyl, 2,3,6-trichlorophenyl, 2,3,4-trichlorophenyl, 3,4,5-tribromophenyl, 2,5,6-tribromophenyl, 2,4,6-tribromophenyl, 1-fluoro-2-naphthyl, 2-fluoro-1-naphthyl, 3-fluoro-1-naphthyl, 2-chloro-1-naphthyl, 1-chloro-2-naphthyl, 2-bromo-1-naphthyl, 3-bromo-1-naphthyl, 2,3-difluoro-1-naphthyl, 3,8-difluoro-1-naphthyl, 4,8-difluoro-1-naphthyl, 5,6-difluoro-1-naphthyl, 2,4- difluoro-1-naphthyl, 2,3-dichloro-1-naphthyl, 3,4-dichloro-1-naphthyl, 4,5-dichloro-1-naphthyl, 5,6-dibromo-1-naphthyl, 2,4-dibromo-1-naphthyl, 2,3,6-trifluoro-1-naphthyl, 2,3,4-trifluoro-1-naphthyl, 3,4,5-trifluoro-1-naphthyl, 4,5,6-trifluoro-1-naphthyl, 2,4,8-trifluoro-1-naphthyl, 2,3,6-trichloro-1-naphthyl, 2,3,4-trichloro-1-naphthyl, 3,4,8-tribromo-1-naphthyl, 4,5,6-tribromo-1-naphthyl and 2,4,6-tribromo-1-naphthyl groups. Examples of aryl groups having at least one lower alkoxy substituent include the 4-methoxyphenyl, 2-methoxyphenyl, 3-methoxyphenyl, 4-ethoxyphenyl, 4-propoxyphenyl, 2-butoxyphenyl, 3-ethoxyphenyl, 3,5-dimethoxyphenyl, 2,5-dimethoxyphenyl, 2,5-dipropoxyphenyl, 2,6-dimethoxyphenyl, 2,4-dimethoxyphenyl, 2,3-diethoxyphenyl, 3,4-diethoxyphenyl, 2,5-diethoxyphenyl, 2,6-diethoxyphenyl, 2,4-dipropoxyphenyl, 2,3,6-trimethoxyphenyl, 2,3,4-trimethoxyphenyl, 3,4,5-trimethoxyphenyl, 2,5,6-methoxyphenyl, 2,4,6-trimethoxyphenyl, 2,3,6-triethoxyphenyl, 2,3,4-triethoxyphenyl, 3,4,5-tripropoxyphenyl, 2,5,6-tripropoxyphenyl, 2,4,6-tripropoxyphenyl, 1-methoxy-2-naphthyl, 2-methoxy-1-naphthyl, 3-methoxy-1-naphthyl, 2-ethoxy-1-naphthyl, 1-ethoxy-2-naphthyl, 2-propoxy-1-naphthyl, 3-propoxy-1-naphthyl, 2,3-dimethoxy-1-naphthyl, 3,8-dimethoxy-1-naphthyl, 4,8-dimethoxy-1-naphthyl, 5,6-dimethoxy-1-naphthyl, 2,4-dimethoxy-1-naphthyl, 2,3-diethoxy-1-naphthyl, 3,4-diethoxy-1-naphthyl, 4,5-diethoxy-1-naphthyl, 5,6-dipropoxy-1-naphthyl, 2,4-dipropoxy-1-naphthyl, 2,3,6-trimethoxy-1-naphthyl, 2,3,4-trimethoxy-1-naphthyl, 3,4,5-trimethoxy-1-naphthyl, 4,5,6-trimethoxy-1-naphthyl, 2,4,8-trimethoxy -1-naphthyl, 2,3,6-triethoxy-1-naphthyl, 2,3,4-triethoxy-1-naphthyl, 3,4,8-tripropoxy-1-naphthyl, 4,5,6-tripropoxy-1-naphthyl and 2,4,6-tripropoxy -1-naphthyl groups. Examples of aryl groups having at least one (and preferably only one) lower alkylenedioxy substituent include the 2,3-methylenedioxyphenyl, 3,4-methylenedioxyphenyl, 2,3-ethylenedioxyphenyl, 3,4-ethylenedioxyphenyl, 2,3-methylenedioxy-1-naphthyl, 3,4-methylenedioxy-1-naphthyl, 5,6-methylenedioxy-1-naphthyl, 6,7-methylenedioxy-1-naphthyl, 7,8-methylenedioxy -1-naphthyl, 3,4-methylenedioxy-2-naphthyl, 5,6-methylenedioxy-2-naphthyl, 6,7-methylenedioxy-2-naphthyl and 7,8-methylenedioxy -2-naphthyl groups. Where the aryl group has two or more substituents, these may, if desired, be selected from two or more different classes of the substituents described above. However, we most prefer either unsubstituted aryl groups or phenyl groups having at least one, and preferably from 1 to 3, substituents selected from the group consisting of lower alkyl groups, halogen atoms, lower alkoxy groups and lower alkylenedioxy groups.

Where $R^4$ or $R^5$ represents an alkyl group, this has from 1 to 6 carbon atoms, and may be a straight or branched chain group. Examples include those listed above as substituents on heterocyclic groups, the $C_1$-$C_4$ alkyl groups being preferred, and the $C_1$-$C_3$ alkyl groups being most preferred. Such alkyl groups may be substituted or unsubstituted, and, if substituted, the substituents are selected from the group consisting of substituents (a), defined above and exemplified in greater detail below. Depending on the nature of the substituent, there is normally no criticality as to the number of substituents, and, as explained in relation to other substituted groups, the only constraint will normally arise from the number of substitutable positions and possibly steric constraints. In general, provided that there are sufficient substitutable positions, the number of substituents will preferably be from 1 to 5, more preferably from 1 to 3. Where the substituent is an aryl group, the number is preferably 1 or 2, and the resulting aralkyl groups are preferably as discussed below.

Where $R^4$ or $R^5$ represents such an aralkyl group, this may optionally be substituted on the aryl ring with one or more of the substituents listed above as substituents (b) or (c), but preferably: lower alkyl groups; halogen atoms; lower alkoxy groups; or lower alkylenedioxy groups. As with the substituents on aryl groups, there is, in principle, no restriction on the number of such substituents, except those dictated by the number of substitutable positions and steric constraints, but we generally find it convenient if, where the group is substituted, there are from 1 to 3 such substituents. The alkyl part is preferably a $C_1$-$C_4$ alkyl group, more preferably a methyl, ethyl or propyl group, which is preferably otherwise unsubstituted. Examples of such aralkyl groups include such unsubstituted aralkyl groups as the benzyl, phenethyl, 1-phenylethyl, 1-phenylpropyl, 2-phenylpropyl, 3-phenylpropyl, 4-phenylbutyl and benzhydryl groups and such substituted aralkyl groups as the chlorobenzyl, methylbenzyl and dimethylbenzyl groups.

Where $R^4$ or $R^5$ represents a $C_3$-$C_{10}$ cycloalkyl group, this may be a monocyclic or polycyclic (e.g. bicyclic or tricyclic) group which may be unsubstituted or may be substituted by at least one $C_1$-$C_4$ alkyl group and may be saturated or have at least one ethylenic carbon-carbon double bond. Included amongst such groups are the simple cycloalkyl groups as well as cyclic terpenyl groups, and, especially in the case of the terpenyl groups, the free valence by which the group is attached to the rest of the molecule may be present on a ring carbon atom or on one of the side chain carbon atoms. Examples of such groups include the cyclopropyl, cyclobutyl, cyclopentyl, cyclohexyl, 8,9,10-trinorbornyl (still commonly known as norbornyl), 3-pinanyl (sometimes known as isopinocamphenyl), 2(3)-pinen-2-yl (sometimes known as myrtamyl) and adamantyl groups, of which those cycloalkyl groups containing from 6 to 10 carbon atoms are preferred.

Where $R^4$ or $R^5$ represents an aromatic heterocyclic group, this has from 5 to 7 ring atoms, and may be substituted or unsubstituted. If substituted, the substituents are selected from the group consisting of substituents (b) and (d), as defined above and exemplified in greater detail below. The group may be monocyclic or fused polycyclic (e.g. bicyclic), and, if it is polycyclic, at least one of the rings (and optionally more than one of the rings) contains at least one hetero-atom selected from the group consisting of nitrogen, oxygen and sulfur hetero-atoms. Examples of such heterocyclic groups include the furyl, thienyl, pyrrolyl, azepinyl, morpholinyl, thiomorpholinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, quinolyl, isoquinolyl, acridyl and tetrahydroacridyl groups. More preferred groups are 5- to 7-membered heterocyclic groups containing at least one nitrogen atom, optionally together with at least one oxygen and/or sulfur atom, such as the pyrrolyl, azepinyl, morpholinyl, thiomorpholinyl, pyrazolyl, imidzaolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl, pyrazinyl, quinolyl, isoquinolyl, acridyl and tetrahydroacridyl groups, the most preferred groups being the imidazolyl, oxazolyl, isoxazolyl, thiazolyl, quinolyl, isoquinolyl, acridyl and tetrahydroacridyl groups.

Where $R^4$ or $R^5$ represents an alkenyl group, this has from 2 to 6 carbon atoms and may be a straight or branched chain group. Examples of such groups include the vinyl, allyl, 1-propenyl, 1-butenyl, 2-butenyl and 3-butenyl groups, of which those alkenyl groups containing from 2 to 4 carbon atoms are preferred.

Where —Y—$R^4$ represents a monocyclic heterocyclic group or a monocyclic heterocyclic group having an aromatic ring fused thereto, the heterocyclic group contains from 4 to 12 hetero-atoms, of which from 1 to 5 are hetero-atoms selected from the group consisting of nitrogen, oxygen and sulfur atoms, and this ring may be monocyclic or polycyclic. The group may be substituted or unsubstituted. If substituted, the substituents are selected from the group consisting of substituents (b) and (d), as defined above and exemplified in greater detail below. If the group is fused with an aromatic ring, the aromatic ring is a heterocyclic or carbocyclic ring having from 6 to 12 ring atoms. Examples of such groups include the 1-pyrrolidinyl, piperidino, 1-tetrahydroquinolyl, tetrahydroisoquinolyl, isoindolyl, indolinyl and 1,3,3-trimethyl-6-azabicyclo[3,2,1]oct-6-yl groups.

Where substituent (a) or (b) is a halogen atom, this is preferably a fluorine, chlorine, bromine or iodine atom.

Where substituent (a) is an alkoxycarbonyl group, the alkyl part thereof is a $C_1$-$C_6$ alkyl group, e.g. as exemplified above in relation to substituents on heterocyclic groups. Specific examples of such alkoxycarbonyl groups include the methoxycarbonyl, ethoxycarbonyl, propoxycarbonyl, isopropoxycarbonyl, butoxycarbonyl, isobutoxycarbonyl and t-butoxycarbonyl groups. The preferred such group is the ethoxycarbonyl group.

Where substituent (a) is an alkoxy group, this may be a straight or branched chain group containing from 1 to 6 carbon atoms, and examples include the methoxy, ethoxy, propoxy, isopropoxy, butoxy, isobutoxy, sec-butoxy, t-butoxy, pentyloxy, isopentyloxy, 2-methylbutoxy, neopentyloxy, hexyloxy, 4-methylpentyloxy, 3-methylpentyloxy, 2-methylpentyloxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy groups.

Where substituent (a) is a heterocyclic group, this may be any one of the aromatic heterocyclic groups, monocyclic heterocyclic groups and monocyclic heterocyclic groups having an aromatic ring fused thereto exemplified in relation to $R^4$ and $R^5$.

Where substituent (a) is an aryloxycarbonyl group or an aralkyloxycarbonyl group where the alkyl part is $C_1$-$C_4$, the aryl or aralkyl part is preferably as defined and exemplified above in relation to the aryl groups which may be represented by $R^4$ and $R^5$.

Where substituent (a) is an aliphatic carboxylic acyl group, this may be a straight or branched chain group, and examples include the formyl, acetyl, propionyl, butyryl, isobutyryl, valeryl, isovaleryl, pivaloyl, hexanoyl, heptanoyl, acryloyl, propioloyl, methacryloyl and crotonoyl groups.

Where substituent (a) is an aromatic carboxylic acyl group, this is an arylcarbonyl group in which the aryl part may be as defined and exemplified above in relation to the aryl groups which may be represented by $R^4$ and $R^5$. Examples include the benzoyl and naphthoyl groups and substituted analogs thereof.

Where substituent (a) is a heterocyclic carboxylic acyl group, this is a heterocyclic-carbonyl group in which the heterocyclic part may be as defined and exemplified above in relation to the heterocyclic groups which may be represented by $R^4$ and $R^5$. Examples include the nicotinoyl and isonicotinoyl groups.

Examples of groups which may be represented by substituent (b) include:

such $C_1$-$C_4$ alkyl groups as the methyl, ethyl, propyl, isopropyl and butyl groups;

the nitro, cyano, hydroxy, mercapto, carbamoyl, thiocarbamoyl, ureido, guanidino, amino and carboxy groups;

$C_1$-$C_4$ alkoxy groups, such as those exemplified above in relation to substituents (a);

aryloxy groups and aralkyloxy groups where the alkyl part is $C_1$-$C_4$, such as those corresponding to the aryl and aralkyl groups exemplified above;

$C_1$-$C_7$ aliphatic carboxylic acyloxy groups, $C_1$-$C_7$ aliphatic carboxylic acylamino groups, aromatic carboxylic acyloxy groups and aromatic carboxylic acylamino groups, such as those corresponding to the acyl groups exemplified above;

$C_1$-$C_4$ alkylthio groups, arylthio groups, aralkylthio groups where the alkyl part is $C_1$-$C_4$, $C_1$-$C_4$ alkylsulfinyl groups, $C_1$-$C_4$ alkylsulfonyl groups, arylsulfinyl groups and arylsulfonyl groups, such as those corresponding to the alkyl and aryl groups exemplified above;

$C_2$-$C_7$ alkoxycarbonylamino groups, aralkyloxycarbonylamino groups, $C_2$-$C_7$ alkoxycarbonyl groups, aryloxycarbonyl groups and aralkyloxycarbonyl groups, such as those corresponding to the alkoxy, aralkyl and aryl groups exemplified above;

$C_1$-$C_7$ aliphatic carboxylic acyl groups, aromatic carboxylic acyl groups and heterocyclic carboxylic acyl groups, such as those exemplified above: alkylcarbamoyl, dialkylcarbamoyl, alkyl(thiocarbamoyl), dialkyl(thiocarbamoyl), alkylureido, dialkylureido, thioureido groups, alkylamino, dialkylamino, hydroxyalkylamino, dihydroxyalkylamino, alkylguanidino, alkyl(thioureido) and dialkyl(thioureido) groups where the alkyl part(s) are as exemplified above;

$C_3$-$C_8$ cycloalkyl groups, such as the cyclopropyl, cyclobutyl, cyclopentyl, cyclohexyl, cycloheptyl and cyclooctyl groups;

$C_5$-$C_8$ cycloalkenyl groups, such as the cyclopentenyl cyclohexenyl cycloheptenyl and cyclooctenyl groups;

aryl groups and heterocyclic groups, such as those exemplified above; and $C_1$-$C_6$ alkyl groups having at least one halogen substituent, such as the chloromethyl, fluoromethyl, trifluoromethyl, 2-iodoethyl, 2,2,2-trichloroethyl and 2,2,2-trifluoroethyl groups.

The compounds of the present invention contain asymmetric carbon atoms in their molecules, and can, therefore, exist in the form of various stereoisomers, in which each of these asymmetric carbon atoms can be in the R- or S- configuration. The individual isomers may be prepared by stereo-specific synthesis techniques, as are well known in the art, or a mixture of isomers may be prepared and then, if desired, separated by well known resolution techniques. Alternatively, the compounds may be employed as mixtures of two or more such isomers. It is well known that pharmacologically active compounds often exhibit greater activity in the form of specific isomers, and, if desired, simple experimentation will reveal which, if any, of the isomers of the compounds of the present invention is the more active.

The compounds of the present invention contain in their molecules certain basic nitrogen atoms and can, therefore, form salts with acids. There is no limitation upon the nature of such salts, provided that, where they are to be used for therapeutic purposes, they are pharmaceutically acceptable, which, as is well-known in the art, means that they do not have reduced activity (or unacceptably reduced activity) or increased toxicity (or unacceptably increased toxicity) compared with the free compound of formula (I). Where, however, they are to be used for non-therapeutic purposes, e.g. as intermediates in the preparation of other compounds, even this limitation does not apply. Examples of suitable acids include: hydrohalic acids (such as hydrofluoric acid hydrochloric acid hydrobromic acid or hydroiodic acid), nitric acid, perchloric acid, sulfuric acid and phosphoric acid: organic sulfonic acids, such as the lower alkylsulfonic acids (e.g. methanesulfonic acid, trifluoromethanesulfonic acid or ethanesulfonic acid) and arylsulfonic acids (e.g. benzenesulfonic acid or p-toluenesulfonic acid); organic carboxylic acids, such as fumaric acid, succinic acid, citric acid, tartaric acid, oxalic acid, maleic acid or the like; and amino acids, such as glutamic acid or aspargic acid.

Preferred classes of compounds of the present invention are those compounds of formula (1) in which:

(A) M represents a saturated heterocyclic group having 6 or 7 ring atoms of which 2 are nitrogen atoms, said group being unsubstituted or having at any of its carbon atoms from 1 to 4 substituents selected from the group consisting of $C_1$-$C_6$ alkyl groups and oxo groups.

(B) M represents a saturated heterocyclic group having 6 or 7 ring atoms of which 2 are nitrogen atoms, said group being unsubstituted or having at any of its carbon atoms 1 or 2 substituents selected from the group consisting of $C_1$-$C_4$ alkyl groups and oxo groups.

(C) M represents a piperazinyl group or a homopiperazinyl group, said group being unsubstituted or having at any of its carbon atoms from 1 to 4 substituents selected from the group consisting of $C_1$-$C_4$ alkyl groups and oxo groups.

(D) M represents a piperazinyl group or a homopiperazinyl group, said group being unsubstituted or having at any of its carbon atoms 1 or 2 substituents selected from the group consisting of $C_1$-$C_4$ alkyl groups and oxo groups.

(E) At least one of $Ar^1$ and $Ar^2$ represents a phenyl group having a halogen substituent at its 4-position.

(F) $R^1$ represents a hydrogen atom or a $C_1$-$C_4$ alkyl group.

(G) $R^1$ represents a hydrogen atom or a $C_1$-$C_2$ alkyl group.

(H) R represents a hydrogen atom or a methyl group.

(I) $R^2$ and $R^3$ together represent an oxo group.

(J) One of $R^4$ and $R^5$ represents a hydrogen atom, a $C_1$-$C_4$ alkyl group or a $C_2$-$C_4$ alkenyl group and the other represents a $C_6$-$C_{10}$ carbocyclic aryl group, an aralkyl group in which the aryl part is $C_6$-$C_{10}$, a $C_6$-$C_{10}$ cycloalkyl group or said aryl or aralkyl group having at least one substituent selected from the group consisting of substituents (b) and (c).

(K) One of $R^4$ and $R^5$ represents a hydrogen atom, a $C_1$-$C_4$ alkyl group or a $C_2$-$C_4$ alkenyl group and the other represents a phenyl group, a benzyl group, a $C_6$-$C_{10}$ cycloalkyl group or said phenyl or benzyl group having at least one substituent selected from the group consisting of substituents (b) and (c).

(L) Both of $X^1$ and $X^2$ represent fluorine atoms.

(M) One of $X^1$ and $X^2$ represents a chlorine atom and the other represents a hydrogen atom.

(N) M represents a saturated heterocyclic group having 6 or 7 ring atoms of which 2 are nitrogen atoms, said group being unsubstituted or having at any of its carbon atoms from 1 to 4 substituents selected from the group consisting of $C_1$-$C_6$ alkyl groups and oxo groups;

at least one of $Ar^1$ and $Ar^2$ represents a phenyl group having a halogen substituent at its 4-position;

$R^1$ represents a hydrogen atom or a $C_1$-$C_6$ alkyl group;

$R^2$ and $R^3$ together represent an oxo group; and one of $R^4$ and $R^5$ represents a hydrogen atom, a $C_1$-$C_4$ alkyl group or a $C_2$-$C_4$ alkenyl group and the other represents a $C_6$-$C_{10}$ carbocyclic aryl group, an aralkyl group in which the aryl part is $C_6$-$C_{10}$, a $C_6$-$C_{10}$ cycloalkyl qroup or said aryl or aralkyl group having at least one substituent selected from the group consisting of substituents (b) and (c).

(O) M represents a saturated heterocyclic group having 6 or 7 ring atoms of which 2 are nitrogen atoms, said group being unsubstituted or having at any of its carbon atoms from 1 to 4 substituents selected from the group consisting of $C_1$-$C_4$ alkyl groups and oxo groups;

at least one of $Ar^1$ and $Ar^2$ represents a phenyl group having a halogen substituent at its 4-position;

$R^1$ represents a hydrogen atom or a $C_1$-$C_4$ alkyl group;

$R^2$ and $R^3$ together represent an oxo group; and one of $R^4$ and $R^5$ represents a hydrogen atom, a $C_1$-$C_4$ alkyl group or a $C_2$-$C_4$ alkenyl group and the other represents a $C_6$-$C_{10}$ carbocyclic aryl group, an aralkyl group in which the aryl part is $C_6$-$C_{10}$, a $C_6$-$C_{10}$ cycloalkyl group or said aryl or aralkyl group having at least one substituent selected from the group consisting of substituents (b) and (c).

(P) M represents a saturated heterocyclic group having 6 or 7 ring atoms of which 2 are nitrogen atoms, said group being unsubstituted or having at any of its carbon atoms 1 or 2 substituents selected from the group consisting of $C_1$-$C_4$ alkyl groups and oxo groups;

at least one of $Ar^1$ and $Ar^2$ represents a phenyl group having a halogen substituent at its 4-position;

$R^1$ represents a hydrogen atom or a $C_1$-$C_4$ alkyl group;

$R^2$ and $R^3$ together represent an oxo group; and one of $R^4$ and $R^5$ represents a hydrogen atom, a $C_1$-$C_4$ alkyl group or a $C_2$-$C_4$ alkenyl group and the other represents a phenyl group, a benzyl group, a $C_6$-$C_{10}$ cycloalkyl group or said phenyl or benzyl group having at least one substituent selected from the group consisting of substituents (b) and (c).

(Q) M represents a saturated heterocyclic group having 6 or 7 ring atoms of which 2 are nitrogen atoms, said group being unsubstituted or having at any of its carbon atoms 1 or 2 substituents selected from the group consisting of $C_1$-$C_4$ alkyl groups and oxo groups;

both of $X^1$ and $X^2$ represent fluorine atoms;

$R^1$ represents a hydrogen atom or a $C_1$-$C_4$ alkyl group;

$R^2$ and $R^3$ together represent an oxo group; and one of $R^4$ and $R^5$ represents a hydrogen atom, a $C_1$-$C_4$ alkyl group or a $C_2$-$C_4$ alkenyl group and the other represents a phenyl group, a benzyl group, a $C_6$-$C_{10}$ cycloalkyl group or said phenyl or benzyl group having at least one substituent selected from the group consisting of substituents (b).

(R) M represents a saturated heterocyclic group having 6 or 7 ring atoms of which 2 are nitrogen atoms, said group being unsubstituted or having at any of its carbon atoms 1 or 2 substituents selected from the group consisting of $C_1$-$C_4$ alkyl groups and oxo groups;

one of $X^1$ and $X^2$ represents a chlorine atom and the other represents a hydrogen atom;

$R^1$ represents a hydrogen atom or a $C_1$-$C_4$ alkyl group;

$R^2$ and $R^3$ together represent an oxo group; and one of $R^4$ and $R^5$ represents a hydrogen atom, a $C_1$-$C_4$ alkyl group or a $C_2$-$C_4$ alkenyl group and the other represents a phenyl group, a benzyl group, a $C_6$-$C_{10}$ cycloalkyl group or said phenyl or benzyl group having at least one substituent selected from the group consisting of substituents (b).

(S) M represents a piperazinyl group or a homopiperazinyl group, said group being unsubstituted or having at any of its carbon atoms from 1 to 4 substituents selected from the group consisting of $C_1$-$C_4$ alkyl groups and oxo groups;

at least one of $Ar^1$ and $Ar^2$ represents a phenyl group having a halogen substituent at its 4-position;

$R^1$ represents a hydrogen atom or a $C_1$-$C_6$ alkyl group;

$R^2$ and $R^3$ together represent an oxo group; and one of $R^4$ and $R^5$ represents a hydrogen atom, a $C_1$-$C_4$ alkyl group or a $C_2$-$C_4$ alkenyl group and the other represents a phenyl group, a benzyl group, a $C_6$-$C_{10}$ cloalkyl group or said phenyl or benzyl group having at least one substituent selected from the group consisting of substituents (b).

(T) M represents a piperazinyl group or a homopiperazinyl group, said group being unsubstituted or having at any of its carbon atoms from 1 to 4 substituents selected from the group consisting of $C_1$-$C_4$ alkyl groups and oxo groups;

at least one of $Ar^1$ and $Ar^2$ represents a phenyl group having a halogen substituent at its 4-position;

$R^1$ represents a hydrogen atom or a $C_1$-$C_4$ alkyl group;

$R^2$ and $R^3$ together represent an oxo group; and one of $R^4$ and $R^5$ represents a hydrogen atom, a $C_1$-$C_4$ alkyl group or a $C_2$-$C_4$ alkenyl group and the other represents a phenyl group, a benzyl group, a $C_6$-$C_{10}$ cycloalkyl group or said phenyl or benzyl group having at least one substituent selected from the group consisting of substituents (b).

(U) M represents a piperazinyl group or a homopiperazinyl group, said group being unsubstituted or having at any of its carbon atoms 1 or 2 substituents selected from the group consisting of $C_1$-$C_4$ alkyl groups and oxo groups;

at least one of $Ar^1$ and $Ar^2$ represents a phenyl group having a halogen substituent at its 4-position; group;

$R^2$ and $R^3$ together represent an oxo group; and one of $R^4$ and $R^5$ represents a hydrogen atom, a $C_1$-$C_4$ alkyl group or a $C_2$-$C_4$ alkenyl group and the other represents a phenyl group, a benzyl group, a $C_6$-$C_{10}$ cycloalkyl group or said phenyl or benzyl group having at least one substituent selected from the group consisting of substituents (b).

(V) M represents a piperazinyl group or a homopiperazinyl group, said group being unsubstituted or having at any of its carbon atoms 1 or 2 substituents selected from the group consisting of $C_1$-$C_4$ alkyl groups and oxo groups;

both of $X^1$ and $X^2$ represent fluorine atoms:

$R^1$ represents a hydrogen atom or a $C_1$-$C_4$ alkyl group;

$R^2$ and $R^3$ together represent an oxo group; and one of $R^4$ and $R^5$ represents a hydrogen atom, a $C_1$-$C_4$ alkyl group or a $C_2$-$C_4$ alkenyl group and the other represents a phenyl group, a benzyl group, a $C_6$-$C_{10}$ cycloalkyl group or said phenyl or benzyl group having at least one substituent selected from the group consisting of substituents (b).

(W) M represents a piperazinyl group or a homopiperazinyl group, said group being unsubstituted or having at any of its carbon atoms 1 or 2 substituents selected from the group consisting of $C_1$-$C_4$ alkyl groups and oxo groups;

one of $X^1$ and $X^2$ represents a chlorine atom and the other represents a hydrogen atom;

$R^1$ represents a hydrogen atom or a $C_1$-$C_4$ alkyl group; $R^2$ and $R^3$ together represent an oxo group; and one of $R^4$ and $R^5$ represents a hydrogen atom, a $C_1$-$C_4$ alkyl group or a $C_2$-$C_4$ alkenyl group and the other represents a phenyl group, a benzyl group, a $C_6$-$C_{10}$ cycloalkyl group or said phenyl or benzyl group having at least one substituent selected from the group consisting of substituents (b).

Examples of specific compounds of the invention are given in the following formulae (I-1) to (I-10), in which the substituents are as defined in the corresponding one of Tables 1 to 10 [i.e. Table 1 relates to formula (I-1), Table 2 relates to formula (I-2) and so on]. In the Tables, the following abbreviations are used:

| | |
|---|---|
| AD | adamantyl. i.e. 1AD is 1-adamantyl and 2AD is 2-adamantyl |
| All | allyl |
| Bu | butyl |
| iBu | isobutyl |
| Bz | benzyl |
| DB | 1,1-dimethylbenzyl |
| DFP | difluorophenyl, i.e. 2,5DFP is 2,5-difluorophenyl, 3,5DFP is 3,5-difluorophenyl and 2,6DFP is 2,6-difluorophenyl |
| DMP | 3,5-dimethoxyphenyl |
| ECM | ethoxycarbonylmethyl |
| Et | ethyl |
| FP | fluorophenyl, i.e. 2FP is 2-fluorophenyl, 3FP is 3-fluorophenyl and 4FP is 4-fluorophenyl |
| Fur | furyl |
| Hx | hexyl |
| cHx | cyclohexyl |
| ID | 2-isoindolyl |
| 4MB | 4-methoxybenzyl |
| MDP | 3,4-methylenedioxyphenyl |
| Me | methyl |
| 4MP | 4-methoxyphenyl |
| Np | naphthyl |
| Pn | pentyl |
| cPn | cyclopentyl |
| 4PP | 4-propoxyphenyl |
| Pr | propyl |
| Pym | pyrimidyl |
| Pyr | pyridyl |
| Pyrd | pyrrolidinyl |
| TAO | N-(1,3,3-trimethyl-6-azabicyclo-[3.2.1]octyl) |
| Thiz | thiazolyl |
| THQ | tetrahydroquinolyl |
| TM | 2,4,6-trimethylphenyl |
| TMP | 3,4,5-trimethoxyphenyl |
| TP | 2,4,5-trimethoxyphenyl |

-continued

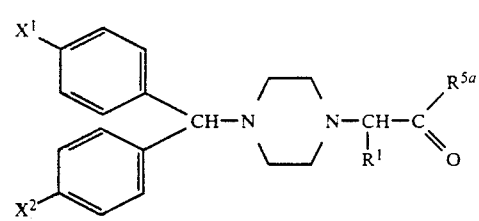 (I-1)

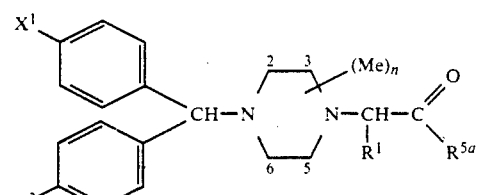 (I-2)

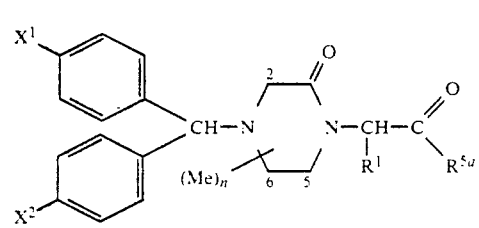 (I-3)

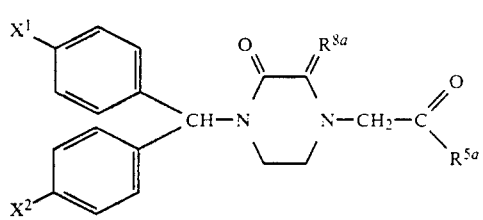 (I-4)

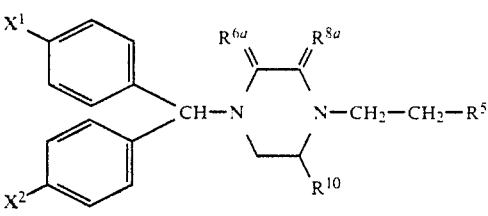 (I-5)

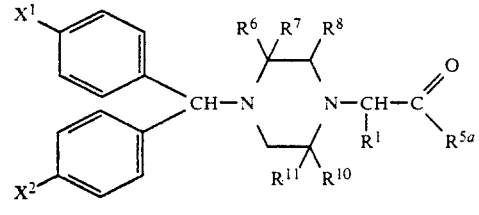 (I-6)

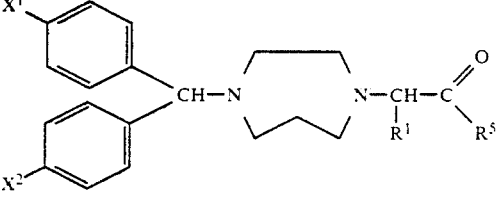 (I-7)

-continued

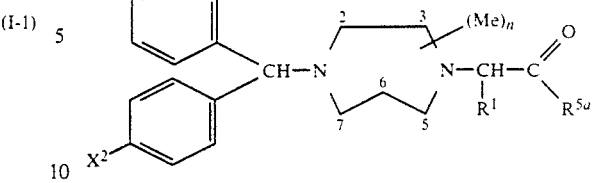 (I-8)

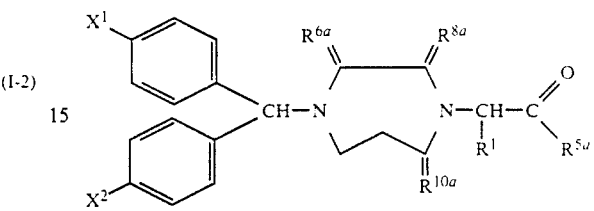 (I-9)

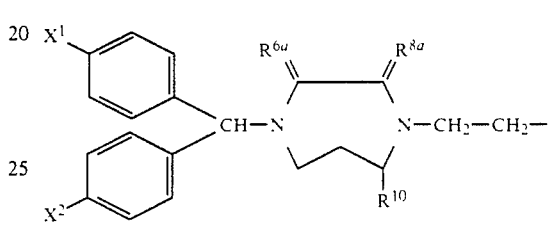 (I-10)

TABLE 1

| CPd No. | X¹ | X² | R¹ | R⁵ᵃ |
|---|---|---|---|---|
| 1-1 | F | F | H | 1-Pyrd |
| 1-2 | F | F | H | THQ |
| 1-3 | F | F | H | TAO |
| 1-4 | F | F | H | DMP-NH |
| 1-5 | F | F | H | 4MP-NH |
| 1-6 | F | F | H | iBu-NH |
| 1-7 | F | F | H | TMP-NH |
| 1-8 | F | F | H | Bz-NH |
| 1-9 | F | F | H | 1-NP-NH |
| 1-10 | F | F | H | cHx-NH |
| 1-11 | F | F | H | TM-NH |
| 1-12 | F | F | H | DB-NH |
| 1-13 | F | F | H | 3FP-NH |
| 1-14 | F | F | H | 2FP-NH |
| 1-15 | F | F | H | 4PP-NH |
| 1-16 | F | F | H | ECM-NH |
| 1-17 | F | F | H | 1AD-NH |
| 1-18 | F | F | H | MDP-NH |
| 1-19 | F | F | H | 2AD-NH |
| 1-20 | F | F | H | 4FP-NH |
| 1-21 | F | F | H | 3,5DFP-NH |
| 1-22 | F | F | H | 2-Pym-NH |
| 1-23 | F | F | H | Et-NH |
| 1-24 | F | F | H | 2-Fur-NH |
| 1-25 | F | F | H | 2-Thiz-NH |
| 1-26 | F | F | H | 2,6DFP-NH |
| 1-27 | F | F | H | 3FP-N-All |
| 1-28 | F | F | H | 3FP-N-Me |
| 1-29 | F | F | H | ID |
| 1-30 | F | F | H | 4MB-NH |
| 1-31 | F | F | H | TP-NH |
| 1-32 | F | F | H | 2,5DFP-NH |
| 1-33 | F | F | H | 2-Pyr-NH |
| 1-34 | F | F | H | cPn-NH |
| 1-35 | F | F | H | 2,4DFP-NH |
| 1-36 | F | F | Me | ID |
| 1-37 | F | F | Me | THQ |
| 1-38 | F | F | Et | TAO |
| 1-39 | F | F | Me | DMP-NH |
| 1-40 | F | F | Bu | 4MP-NH |
| 1-41 | F | F | Me | 1-NP-NH |
| 1-42 | F | F | Me | TM-NH |
| 1-43 | F | F | Et | DB-NH |
| 1-44 | F | F | Me | 3FP-NH |
| 1-45 | F | F | Bu | 2FP-NH |

TABLE 1-continued

| CPd No. | X¹ | X² | R¹ | R$^{5a}$ |
|---|---|---|---|---|
| 1-46 | F | F | Pn | 4PP-NH |
| 1-47 | F | F | Hx | ECM-NH |
| 1-48 | F | F | Me | IAD-NH |
| 1-49 | F | F | Me | 3,5DFP-NH |
| 1-50 | F | F | Me | 2-Pym-NH |
| 1-51 | F | F | Me | Et-NH |
| 1-52 | F | F | Me | 2-Fur-NH |
| 1-53 | F | F | Me | 2-Thiz-NH |
| 1-54 | F | F | Me | 2,6DFP-NH |
| 1-55 | F | F | Me | 3FP-N-All |
| 1-56 | F | F | Me | 3FP-N-Me |
| 1-57 | F | F | Me | ID |
| 1-58 | F | F | Me | 4MB-NH |
| 1-59 | F | F | Me | 1-Np-NH |
| 1-60 | F | F | Me | TP-NH |
| 1-61 | F | F | Me | 2,5DFP-NHO |
| 1-62 | F | F | Me | 2-Pyr-NH |
| 1-63 | F | F | Me | cPn-NH |
| 1-64 | F | F | Me | 2,4DFP-NH |
| 1-65 | Cl | H | H | 1-Pyrd |
| 1-66 | Cl | H | H | THQ |
| 1-67 | Cl | H | H | TAO |
| 1-68 | Cl | H | H | DMP-NH |
| 1-69 | Cl | H | H | 4MP-NH |
| 1-70 | Cl | H | H | iBu-NH |
| 1-71 | Cl | H | H | TMP-NH |
| 1-72 | Cl | H | H | Bz-NH |
| 1-73 | Cl | H | H | 1-NP-NH |
| 1-74 | Cl | H | H | cHx-NH |
| 1-75 | Cl | H | H | TM-NH |
| 1-76 | Cl | H | H | DB-NH |
| 1-77 | Cl | H | H | 3FP-NH |
| 1-78 | Cl | H | H | 2FP-NH |
| 1-79 | Cl | H | H | 4PP-NH |
| 1-80 | Cl | H | H | ECM-NH |
| 1-81 | Cl | H | H | IAD-NH |
| 1-82 | Cl | H | H | MDP-NH |
| 1-83 | Cl | H | H | 2AD-NH |
| 1-84 | Cl | H | H | 4FP-NH |
| 1-85 | Cl | H | H | 3,5DFP-NH |
| 1-86 | Cl | H | H | 2-Pym-NH |
| 1-87 | Cl | H | H | Et-NH |
| 1-88 | Cl | H | H | 2-Fur-NH |
| 1-89 | Cl | H | H | 2-Thiz-NH |
| 1-90 | Cl | H | H | 2,6DFP-NH |
| 1-91 | Cl | H | H | 3FP-N-All |
| 1-92 | Cl | H | H | 3FP-N-Me |
| 1-93 | Cl | H | H | ID |
| 1-94 | Cl | H | H | 4MB-NH |
| 1-95 | Cl | H | H | 1-NP-NH |
| 1-96 | Cl | H | H | TP-NH |
| 1-97 | Cl | H | H | 2,5DFP-NH |
| 1-98 | Cl | H | H | 2-Pyr-NH |
| 1-99 | Cl | H | H | cPn-NH |
| 1-100 | Cl | H | H | 2,4DFP-NH |
| 1-101 | Cl | H | Me | 1-Pyrd |
| 1-102 | Cl | H | Me | THQ |
| 1-103 | Cl | H | Et | TAO |
| 1-104 | Cl | H | Pr | DMP-NH |
| 1-105 | Cl | H | Bu | 4MP-NH |
| 1-106 | Cl | H | Pn | iBu-NH |
| 1-107 | Cl | H | Hx | TMP-NH |
| 1-108 | Cl | H | Et | DB-NH |
| 1-109 | Cl | H | Pr | 3FP-NH |
| 1-110 | Cl | H | Bu | 2FP-NH |
| 1-111 | Cl | H | Pn | 4PP-NH |
| 1-112 | Cl | H | Hx | ECM-NH |
| 1-113 | Cl | H | Me | 3,5DFP-NH |
| 1-114 | Cl | H | Me | 2-Pym-NH |
| 1-115 | Cl | H | Me | Et-NH |
| 1-116 | Cl | H | Me | 2-Fur-NH |
| 1-117 | Cl | H | Me | 2-Thiz-NH |
| 1-118 | Cl | H | Me | 2,6DFP-NH |
| 1-119 | Cl | H | Me | 3FP-N-All |
| 1-120 | Cl | H | Me | 3FP-N-Me |
| 1-121 | Cl | H | Me | ID |
| 1-122 | Cl | H | Me | 4MB-NH |
| 1-123 | Cl | H | Me | 1-NP-NH |
| 1-124 | Cl | H | Me | 2,5DFP-NH |
| 1-125 | Cl | H | Me | 2-Pyr-NH |
| 1-126 | Cl | H | Me | cPn-NH |
| 1-127 | Cl | H | Me | 2,4DFP-NH |

TABLE 2

| Cpd No. | X¹ | X² | R¹ | R$^{5a}$ | n | position of (Me)$_n$ |
|---|---|---|---|---|---|---|
| 2-1 | F | F | Me | 2FP-NH | 2 | 2,5 |
| 2-2 | F | F | Me | TM-NH | 2 | 2,5 |
| 2-3 | F | F | H | 3FP-NH | 1 | 2 |
| 2-4 | F | F | H | 1-Pyrd | 1 | 2 |
| 2-5 | F | F | H | IAD-NH | 2 | 2,5 |
| 2-6 | F | F | H | TAO | 1 | 3 |
| 2-7 | F | F | H | 4MP-NH | 2 | 2,5 |
| 2-8 | F | F | H | TM-NH | 2 | 2,5 |
| 2-9 | F | F | H | TMP-NH | 2 | 2,5 |
| 2-10 | F | F | H | 2,5DFP-NH | 2 | 2,5 |
| 2-11 | F | F | H | TM-NH | 1 | 3 |
| 2-12 | F | F | H | 3FP-NH | 1 | 3 |
| 2-13 | F | F | H | TMP-NH | 1 | 3 |
| 2-14 | F | F | H | 2FP-NH | 1 | 3 |
| 2-15 | F | F | H | 4FP-NH | 1 | 3 |
| 2-16 | F | F | H | 2FP-NH | 2 | 2,5 |
| 2-17 | F | F | H | 1-Np-NH | 2 | 2,5 |
| 2-18 | F | F | H | cHx-NH | 3 | 2,2,3 |
| 2-19 | F | F | H | 3FP-NH | 2 | 3,3 |
| 2-20 | F | F | H | DB-NH | 4 | 2,3,5,6 |
| 2-21 | F | F | H | 3FP-NH | 2 | 2,5 |
| 2-22 | F | F | H | 4FP-NH | 2 | 2,5 |
| 2-23 | F | F | H | 4PP-NH | 2 | 2,5 |
| 2-24 | F | F | H | ECM-NH | 2 | 2,5 |
| 2-25 | Cl | H | H | 1-Pyrd | 1 | 2 |
| 2-26 | Cl | H | H | THQ | 2 | 2,2 |
| 2-27 | Cl | H | H | TAO | 3 | 2,2,5 |
| 2-28 | Cl | H | H | DMP-NH | 4 | 2,2,5,5 |
| 2-29 | Cl | H | H | 4MP-NH | 2 | 2,5 |
| 2-30 | Cl | H | H | iBu-NH | 3 | 2,5,5 |
| 2-31 | Cl | H | H | TMP-NH | 2 | 5,5 |
| 2-32 | Cl | H | H | Bz-NH | 2 | 2,3 |
| 2-33 | Cl | H | H | 1-Np-NH | 1 | 3 |
| 2-34 | Cl | H | H | cHx-NH | 3 | 2,2,3 |
| 2-35 | Cl | H | H | TM-NH | 4 | 2,2,3,3 |
| 2-36 | Cl | H | H | DB-NH | 4 | 2,3,5,6 |
| 2-37 | F | Cl | H | 1-Pyrd | 1 | 2 |
| 2-38 | F | Cl | H | THQ | 2 | 2,2 |
| 2-39 | F | Br | H | TAO | 3 | 2,2,5 |
| 2-40 | F | Cl | H | DMP-NH | 4 | 2,2,5,5 |
| 2-41 | F | H | H | 4MP-NH | 2 | 2,5 |
| 2-42 | F | H | H | iBu-NH | 3 | 2,5,5 |
| 2-43 | F | Cl | H | TMP-NH | 2 | 5,5 |
| 2-44 | F | Br | H | Bz-NH | 2 | 2,3 |
| 2-45 | F | H | H | 1-Np-NH | 1 | 3 |
| 2-46 | F | Cl | H | cHx-NH | 3 | 2,2,3 |
| 2-47 | F | Br | H | TM-NH | 4 | 2,2,3,3 |
| 2-48 | F | H | H | DB-NH | 4 | 2,3,5,6 |
| 2-49 | Cl | Cl | H | 1-Pyrd | 1 | 2 |
| 2-50 | Cl | Cl | H | THQ | 2 | 2,2 |
| 2-51 | Cl | Br | H | TAO | 3 | 2,2,5 |
| 2-52 | Cl | Cl | H | DMP-NH | 4 | 2,2,5,5 |
| 2-53 | Cl | Cl | H | 4MP-NH | 2 | 2,5 |
| 2-54 | Cl | Br | H | iBu-NH | 3 | 2,5,5 |
| 2-55 | Cl | Cl | H | TMP-NH | 2 | 5,5 |
| 2-56 | Cl | Cl | H | Bz-NH | 2 | 2,3 |
| 2-57 | Cl | Br | H | 1-Np-NH | 1 | 3 |
| 2-58 | Cl | Cl | H | cHx-NH | 3 | 2,2,3 |
| 2-59 | Cl | Cl | H | TM-NH | 4 | 2,2,3,3 |
| 2-60 | Cl | Cl | H | DB-NH | 4 | 2,3,5,6 |
| 2-61 | F | F | Et | 3FP-NH-All | 3 | 2,2,3 |
| 2-62 | F | F | Me | TM-NH | 1 | 3 |
| 2-63 | F | F | Me | 2,6DFP-NH | 1 | 3 |
| 2-64 | F | F | Me | 1-Np-NH | 1 | 3 |
| 2-65 | F | F | Me | 3FP-NH-Me | 4 | 2,2,3,3 |
| 2-66 | F | H | Me | 2,5DFP-NH | 3 | 2,3,3 |
| 2-67 | Cl | Cl | Et | 2-Pyr-NH | 3 | 2,3,5 |

TABLE 3

| Cpd No. | X¹ | X² | R¹ | R⁵ᵃ | n | position of (Me)ₙ |
|---|---|---|---|---|---|---|
| 3-1 | F | F | H | 1AD-NH | 1 | 2 |
| 3-2 | F | F | H | TM-NH | 0 | — |
| 3-3 | Cl | H | H | 2FP-NH | 0 | — |
| 3-4 | Cl | H | H | ECM-NH | 1 | 2 |
| 3-5 | Cl | H | H | 1AD-NH | 2 | 2,5 |
| 3-6 | F | H | H | 2FP-NH | 0 | — |
| 3-7 | F | H | H | ECM-NH | 1 | 2 |
| 3-8 | F | Cl | H | 1AD-NH | 2 | 2,5 |
| 3-9 | F | F | Me | TM-NH | 0 | — |
| 3-10 | F | F | Me | 1AD-NH | 0 | — |
| 3-11 | F | F | Me | 3FP-NH | 0 | — |

TABLE 4

| Cpd No. | X¹ | X² | R⁵ᵃ | R⁸ᵃ |
|---|---|---|---|---|
| 4-1 | Cl | H | 3FP-NH | H₂ |
| 4-2 | Cl | H | 4PP-NH | O |
| 4-3 | F | Cl | 3FP-NH | H₂ |
| 4-4 | F | H | 4PP-NH | O |

TABLE 5

| Cpd No. | X¹ | X² | R⁵ᵃ | R⁶ᵃ | R⁸ᵃ | R¹⁰ |
|---|---|---|---|---|---|---|
| 5-1 | Cl | Br | 3FP-NH | O | H₂ | H |
| 5-2 | Cl | Cl | 2FP-NH | H₂ | O | H |
| 5-3 | Cl | Cl | 4PP-NH | O | O | H |
| 5-4 | Cl | Br | ECM-NH | Me, H | O | H |
| 5-5 | Cl | Cl | 1AD-NH | Me, H | O | Me |
| 5-6 | Cl | Cl | MDP-NH | H₂ | H₂ | H |
| 5-7 | F | Cl | 2AD-NH | H₂ | H₂ | H |
| 5-8 | F | F | 4FP-NH | H₂ | H₂ | H |
| 5-9 | F | F | 3FP-NH | H₂ | H₂ | H |
| 5-10 | F | F | 4MP-NH | Me, H | H₂ | Me |
| 5-11 | F | F | 1-Np-NH | H₂ | H₂ | H |

TABLE 6

| Cpd No. | X¹ | X² | R¹ | R⁵ᵃ | R⁶ | R⁷ | R⁸ | R¹⁰ | R¹¹ |
|---|---|---|---|---|---|---|---|---|---|
| 6-1 | F | F | Et | ID | Et | H | H | Me | H |
| 6-2 | Cl | H | Et | 4MB-NH | H | H | H | Me | H |
| 6-3 | Cl | H | Me | 1-Np-NH | H | H | H | Pr | Me |
| 6-4 | Cl | H | Me | TP-NH | Me | Me | H | Et | Me |
| 6-5 | F | H | Et | cPn-NH | Et | H | H | H | H |
| 6-6 | Cl | H | Me | 2,4DFP-NH | Et | H | Et | H | H |

TABLE 7

| Cpd No. | X¹ | X² | R¹ | R⁵ᵃ |
|---|---|---|---|---|
| 7-1 | F | F | H | 1-Pyrd |
| 7-2 | F | F | H | THQ |
| 7-3 | F | F | H | TAO |
| 7-4 | F | F | H | DMP-N |
| 7-5 | F | F | H | 4MP-NH |
| 7-6 | F | F | H | iBu-NH |
| 7-7 | F | F | H | TMP-NH |
| 7-8 | F | F | H | Bz-NH |
| 7-9 | F | F | H | 1-NP-NH |
| 7-10 | F | F | H | cHx-NH5 |
| 7-11 | F | F | H | TM-NH |
| 7-12 | F | F | H | DB-NH |
| 7-13 | F | F | H | 3FP-NH |
| 7-14 | F | F | H | 2FP-NH |
| 7-15 | F | F | H | 4PP-NH |
| 7-16 | F | F | H | ECM-NH |
| 7-17 | F | F | H | 1AD-NH |
| 7-18 | F | F | H | MDP-NH |
| 7-19 | F | F | H | 2AD-NH |
| 7-20 | F | F | H | 4FP-NH |
| 7-21 | F | F | H | 3,5DFP-NH |
| 7-22 | F | F | H | 2-Pym-NH |
| 7-23 | F | F | H | Et-NH |
| 7-24 | F | F | H | 2-Fur-NH |
| 7-25 | F | F | H | 2-Thiz-NH |
| 7-26 | F | F | H | 2,6DFP-NH |
| 7-27 | F | F | H | 3FP-N-All |
| 7-28 | F | F | H | 3FP-N-Me |
| 7-29 | F | F | H | ID |
| 7-30 | F | F | H | 4MB-NH |
| 7-31 | F | F | H | 1-Np-NH |
| 7-32 | F | F | H | TP-NH |
| 7-33 | F | F | H | 2,5DFP-NH |
| 7-34 | F | F | H | 2-Pyr-NH |
| 7-35 | F | F | H | cPn-NH |
| 7-36 | F | F | H | 2,4DFP-NH |
| 7-37 | F | F | Me | 1-Pyrd |
| 7-38 | F | F | Me | THQ |
| 7-39 | F | F | Et | TAO |
| 7-40 | F | F | Me | DMP-NH |
| 7-41 | F | F | Bu | 4MP-NH |
| 7-42 | F | F | Pn | iBu-NH |
| 7-43 | F | F | Hx | TMP-NH |
| 7-44 | F | F | Me | 1-Np-NH |
| 7-45 | F | F | Me | TM-NH |
| 7-46 | F | F | Et | DB-NH |
| 7-47 | F | F | Pr | 3FP-NH |
| 7-48 | F | F | Bu | 4FP-NH |
| 7-49 | F | F | Bu | 2FP-NH |
| 7-50 | F | F | Pn | 4PP-NH |
| 7-51 | F | F | Hx | ECM-NH |
| 7-52 | F | F | Me | 1AD-NH |
| 7-53 | F | F | Me | 3,5DFP-NH |
| 7-54 | F | F | Me | 2-Pym-NH |
| 7-55 | F | F | Me | Et-NH |
| 7-56 | F | F | Me | 2-Fur-NH |
| 7-57 | F | F | Me | 2-Thiz-NH |
| 7-58 | F | F | Me | 2,6DFP-NH |
| 7-59 | F | F | Me | 3FP-N-All |
| 7-60 | F | F | Me | 3FP-N-Me |
| 7-61 | F | F | Me | ID |
| 7-62 | F | F | Me | 4MB-NH |
| 7-63 | F | F | Me | 1-Np-NH |
| 7-64 | F | F | Me | TP-NH |
| 7-65 | F | F | Me | 2,5DFP-NH |
| 7-66 | F | F | Me | 2-Pyr-NH |
| 7-67 | F | F | Me | cPn-NH |
| 7-68 | F | F | Me | 2,4DFP-NH |
| 7-69 | F | F | Me | 2,5DFP-NH |
| 7-70 | Cl | H | H | 1-Pyrd |
| 7-71 | Cl | H | H | THQ |
| 7-72 | Cl | H | H | TAO |
| 7-73 | Cl | H | H | DMP-NH |
| 7-74 | Cl | H | H | 4MP-NH |
| 7-75 | Cl | H | H | iBu-NH |
| 7-76 | Cl | H | H | TMP-NH |
| 7-77 | Cl | H | H | Bz-NH |
| 7-78 | Cl | H | H | 1-NP-NH |
| 7-79 | Cl | H | H | cHx-NH |
| 7-80 | Cl | H | H | TM-NH |
| 7-81 | Cl | H | H | DB-NH |
| 7-82 | Cl | H | H | 3FP-NH |
| 7-83 | Cl | H | H | 2FP-NH |
| 7-84 | Cl | H | H | 4PP-NH |
| 7-85 | Cl | H | H | ECM-NH |
| 7-86 | Cl | H | H | 1AD-NH |
| 7-87 | Cl | H | H | MDP-NH |
| 7-88 | Cl | H | H | 2AD-NH |
| 7-89 | Cl | H | H | 4FP-NH |
| 7-90 | Cl | H | H | 3,5DFP-NH |
| 7-91 | Cl | H | H | 2-Pym-NH |
| 7-92 | Cl | H | H | Et-NH |
| 7-93 | Cl | H | H | 2-Fur-NH |
| 7-94 | Cl | H | H | 2-Thiz-NH |
| 7-95 | Cl | H | H | 2,6DFP-NH |
| 7-96 | Cl | H | H | 3FP-N-All |
| 7-97 | Cl | H | H | 3FP-N-Me |
| 7-98 | Cl | H | H | ID |
| 7-99 | Cl | H | H | 4MB-NH |
| 7-100 | Cl | H | H | 1-Np-NH |
| 7-101 | Cl | H | H | TP-NH |
| 7-102 | Cl | H | H | 2,5DFP-NH |

TABLE 7-continued

| CPd No. | X¹ | X² | R¹ | R⁵ᵃ |
|---|---|---|---|---|
| 7-103 | Cl | H | H | 2-Pyr-NH |
| 7-104 | Cl | H | H | cPn-NH |
| 7-105 | Cl | H | H | 2,4DFP-NH |
| 7-106 | Cl | H | Me | 1-Pyrd |
| 7-107 | Cl | H | Me | THQ |
| 7-108 | Cl | H | Et | TAO |
| 7-109 | Cl | H | Pr | DMP-NH |
| 7-110 | Cl | H | Bu | 4MP-NH |
| 7-111 | Cl | H | Pn | iBu-NH |
| 7-112 | Cl | H | Hx | TMP-NH |
| 7-113 | Cl | H | Et | DB-NH |
| 7-114 | Cl | H | Pr | 3FP-NH |
| 7-115 | Cl | H | Bu | 2FP-NH |
| 7-116 | Cl | H | Pn | 4PP-NH |
| 7-117 | Cl | H | Hx | ECM-NH |
| 7-118 | Cl | H | Me | 3,5DFP-NH |
| 7-119 | Cl | H | Me | 2-Pym-NH |
| 7-120 | Cl | H | Me | Et-NH |
| 7-121 | Cl | H | Me | 2-Fur-NH |
| 7-122 | Cl | H | Me | 2-Thiz-NH |
| 7-123 | Cl | H | Me | 2,6DFP-NH |
| 7-124 | Cl | H | Me | 3FP-N-All |
| 7-125 | Cl | H | Me | 3FP-N-Me |
| 7-126 | Cl | H | Me | ID |
| 7-127 | Cl | H | Me | 4MB-NH |
| 7-128 | Cl | H | Me | 1-Np-NH |
| 7-129 | Cl | H | Me | TP-NH |
| 7-130 | Cl | H | Me | 2,5DFP-NH |
| 7-131 | Cl | H | Me | 2-Pyr-NH |
| 7-132 | Cl | H | Me | cPn-NH |
| 7-133 | Cl | H | Me | 2,4DFP-NH |

TABLE 8

| CPd No. | X¹ | X² | R¹ | R⁵ᵃ | n | position of (Me)ₙ |
|---|---|---|---|---|---|---|
| 8-1 | F | F | H | 1-Pyrd | 1 | 2 |
| 8-2 | F | F | H | THQ | 2 | 2,2 |
| 8-3 | F | F | H | TAO | 3 | 2,2,5 |
| 8-4 | F | F | H | DMP-NH | 4 | 2,2,5,5 |
| 8-5 | F | F | H | 4MP-NH | 2 | 2,5 |
| 8-6 | F | F | H | iBu-NH | 3 | 2,5,5 |
| 8-7 | F | F | H | TMP-NH | 2 | 5,5 |
| 8-8 | F | F | H | Bz-NH | 2 | 2,3 |
| 8-9 | F | F | H | 1-Np-NH | 1 | 3 |
| 8-10 | F | F | H | cHx-NH | 3 | 2,2,3 |
| 8-11 | F | F | H | TM-NH | 4 | 2,2,3,3 |
| 8-12 | F | F | H | DB-NH | 4 | 2,3,5,7 |
| 8-13 | Cl | H | H | 1-Pyrd | 1 | 2 |
| 8-14 | Cl | H | H | THQ | 2 | 2,2 |
| 8-15 | Cl | H | H | TAO | 3 | 2,2,5 |
| 8-16 | Cl | H | H | DMP-NH | 4 | 2,2,5,5 |
| 8-17 | Cl | H | H | 4MP-NH | 2 | 2,5 |
| 8-18 | Cl | H | H | iBu-NH | 3 | 2,5,5 |
| 8-19 | Cl | H | H | TMP-NH | 2 | 5,5 |
| 8-20 | Cl | H | H | Bz-NH | 2 | 2,3 |
| 8-21 | Cl | H | H | 1-Np-NH | 1 | 3 |
| 8-22 | Cl | H | H | cHx-NH | 3 | 2,2,3 |
| 8-23 | Cl | H | H | TM-NH | 4 | 2,2,3,3 |
| 8-24 | Cl | H | H | DB-NH | 4 | 2,3,5,7 |
| 8-25 | F | Cl | H | 1-Pyrd | 1 | 2 |
| 8-26 | F | Cl | H | THQ | 2 | 2,2 |
| 8-27 | F | Br | H | TAO | 3 | 2,2,5 |
| 8-28 | F | Cl | H | DMP-NH | 4 | 2,2,5,5 |
| 8-29 | F | H | H | 4MP-NH | 2 | 2,5 |
| 8-30 | F | H | H | iBu-NH | 3 | 2,5,5 |
| 8-31 | F | Cl | H | TMP-NH | 2 | 5,5 |
| 8-32 | F | Br | H | Bz-NH | 2 | 2,3 |
| 8-33 | F | H | H | 1-Np-NH | 1 | 3 |
| 8-34 | F | Cl | H | cHx-NH | 3 | 2,2,3 |
| 8-35 | F | Br | H | TM-NH | 4 | 2,2,3,3 |
| 8-36 | F | H | H | DB-NH | 4 | 2,3,5,7 |
| 8-37 | Cl | Cl | H | 1-Pyrd | 1 | 2 |
| 8-38 | Cl | Cl | H | THQ | 2 | 2,2 |
| 8-39 | Cl | Br | H | TAO | 3 | 2,2,5 |
| 8-40 | Cl | Cl | H | DMP-NH | 4 | 2,2,5,5 |
| 8-41 | Cl | Cl | H | 4MP-NH | 2 | 2,5 |
| 8-42 | Cl | Br | H | iBu-NH | 3 | 2,5,5 |

TABLE 8-continued

| CPd No. | X¹ | X² | R¹ | R⁵ᵃ | n | position of (Me)ₙ |
|---|---|---|---|---|---|---|
| 8-43 | Cl | Cl | H | TMP-NH | 2 | 5,5 |
| 8-44 | Cl | Cl | H | Bz-NH | 2 | 2,3 |
| 8-45 | Cl | Br | H | 1-Np-NH | 1 | 3 |
| 8-46 | Cl | Cl | H | cHx-NH | 3 | 2,2,3 |
| 8-47 | Cl | Cl | H | TM-NH | 4 | 2,2,3,3 |
| 8-48 | Cl | Cl | H | DB-NH | 4 | 2,3,5,7 |
| 8-49 | F | F | Et | 2-Thiz-NH | 2 | 2,2 |
| 8-50 | F | F | Me | 2,6DFP-NH | 2 | 2,3 |
| 8-51 | F | F | Et | 3FP-N-All | 3 | 2,2,3 |
| 8-52 | F | F | Me | 3FP-N-Me | 4 | 2,2,3,3 |
| 8-53 | Cl | H | Et | 4MB-NH | 1 | 5 |
| 8-54 | F | H | Me | 2,5DFP-NH | 3 | 2,3,3 |
| 8-55 | Cl | Cl | Et | 2-Pyr-NH | 3 | 2,3,5 |
| 8-56 | F | F | H | 3FP-NH | 1 | 2 |

TABLE 9

| CPd No. | X¹ | X² | R¹ | R⁵ᵃ | R⁶ᵃ | R⁸ᵃ | R¹⁰ᵃ |
|---|---|---|---|---|---|---|---|
| 9-1 | F | F | H | 3FP-NH | O | H,H | H,H |
| 9-2 | F | F | H | 2FP-NH | H,H | O | H,H |
| 9-3 | F | F | H | 4PP-NH | O | O | H,H |
| 9-4 | F | F | H | ECM-NH | Me,H | O | H,H |
| 9-5 | F | F | H | 1AD-NH | Me,H | O | Me,H |
| 9-6 | Cl | H | H | 3FP-NH | O | H,H | H,H |
| 9-7 | Cl | H | H | 2FP-NH | H,H | O | H,H |
| 9-8 | Cl | H | H | 4PP-NH | O | O | H,H |
| 9-9 | Cl | H | H | ECM-NH | Me,H | O | H,H |
| 9-10 | Cl | H | H | 1AD-NH | Me,H | O | Me,H |
| 9-11 | F | Cl | H | 3FP-NH | O | H,H | H,H |
| 9-12 | F | H | H | 2FP-NH | H,H | O | H,H |
| 9-13 | F | H | H | 4PP-NH | O | O | H,H |
| 9-14 | F | H | H | ECM-NH | Me,H | O | H,H |
| 9-15 | F | Cl | H | 1AD-NH | Me,H | O | Me,H |
| 9-16 | F | F | Me | 2-Fur-NH | Et,H | H,H | H,H |
| 9-17 | F | F | Et | ID | Et,H | H,H | Me,H |
| 9-18 | Cl | H | Me | 1-Np-NH | H,H | H,H | Pr,Me |
| 9-19 | Cl | H | Me | TP-NH | Me,Me | H,H | Et,Me |
| 9-20 | F | H | Et | cPn-NH | Et,H | H,H | H,H |
| 9-21 | Cl | H | Me | 2,4DFP-NH | Et,H | Et,H | H,H |

TABLE 10

| CPd No. | X¹ | X² | R⁵ᵃ | R⁶ᵃ | R⁸ᵃ | R¹⁰ |
|---|---|---|---|---|---|---|
| 10-1 | Cl | Br | 3FP-NH | O | H,H | H |
| 10-2 | Cl | Cl | 2FP-NH | H,H | O | H |
| 10-3 | Cl | Cl | 4PP-NH | O | O | H |
| 10-4 | Cl | Br | ECM-NH | Me,H | O | H |
| 10-5 | Cl | Cl | 1AD-NH | Me,H | O | Me |
| 10-6 | Cl | Cl | MDP-NH | H,H | H,H | H |
| 10-7 | F | Cl | 2AD-NH | H,H | H,H | H |
| 10-8 | F | F | 4FP-NH | H,H | H,H | H |
| 10-9 | F | F | 3,5DFP-NH | H,H | H,H | H |
| 10-10 | F | F | 2-Pym-NH | H,H | H,H | H |
| 10-11 | F | F | Et-NH | H,H | H,H | H |

Of the compounds listed above, the following are preferred, that is to say Compounds No. 1-1, 1-2, 1-3, 1-4, 1-5, 1-6, 1-7, 1-8, 1-9, 1-10, 1-12, 1-13, 1-14, 1-15, 1-16, 1-17, 1-18, 1-19, 1-20, 1-21, 1-26, 1-27, 1-28, 1-29, 1-36, 1-37, 1-39, 1-40, 1-41, 1-42, 1-44, 1-48, 1-49, 1-53, 1-54, 1-55, 1-56, 1-57, 1-59, 1-66, 1-69, 1-75, 1-76, 1-77, 1-81, 1-91, 1-92, 1-93, 1-102, 1-105, 1-108, 1-109, 1-113, 1-119, 1-120, 1-121, 2-1, 2-2, 2-5, 2-6, 3-1, 2-7, 2-8, 2-9, 2-10, 2-13, 2-14, 2-15, 2-16, 2-17, 2-19, 2-21, 2-22, 2-26, 2-29, 2-35, 2-38, 2-41, 2-47, 2-50, 2-53, 2-59, 2-61, 2-62, 2-63, 2-64, 2-65, 3-2, 3-5, 3-8, 3-9, 3-10, 3-11, 4-3, 5-1, 5-5, 5-8, 5-9, 5-10, 5-11, 6-1, 7-1, 7-2, 7-3, 7-5, 7-6, 7-7, 7-8, 7-10, 7-11, 7-12, 7-13, 7-14, 7-15, 7-16, 7-17, 7-18, 7-26, 7-27, 7-28, 7-30, 7-38, 7-40, 7-41, 7-44, 7-45, 7-47, 7-52, 7-59, 7-60, 7-61, 7-63, 7-71, 7-74, 7-80, 7-82, 7-86, 7-96, 7-97, 7-98, 7-107, 7-110, 7-114, 7-124, 7-125, 7-126, 8-2, 8-5, 8-11, 8-14, 8-17, 8-23, 8-24, 8-26, 8-29, 8-35, 8-36, 8-38, 8-41, 8-48, 8-51, 8-52, 9-1, 9-5, 9-15 and 9-17. Of these, the more preferred compounds are Compounds No. 1-5, 1-7, 1-11, 1-12, 1-13, 1-26, 1-27, 1-28, 1-37, 1-44, 1-48, 1-69, 1-75, 1-77, 2-5, 2-7, 2-8, 2-11, 2-12, 2-19, 2-21, 5-8, 2-62, 7-5, 7-11, 7-12, 7-13, 7-17, 7-30, 7-38, 7-45 and 7-52. The most preferred compounds are:

1-11. 1-[Bis(4-fluorophenyl)methyl]-4-(2,4,6-trimethylphenylcarbamoylmethyl)piperazine:

1-12. 1-[Bis(4-fluorophenyl)methyl]-4-(1,1-dimethylbenzylcarbamoylmethyl)piperazine;

1-13. 1-[Bis(4-fluorophenyl)methyl]-4-(3-fluorophenylcarbamoylmethyl)piperazine;

1-27. 1-[Bis(4-fluorophenyl)methyl]-4-[N-allyl-N-(3-fluorophenyl)carbamoylmethyl]piperazine;

1-37. 1-[Bis(4-fluorophenyl)methyl]-4-[1-(1,2,3,4-tetrahydroquinoline-1-carbonyl)ethyl]piperazine;

1-44. 1-[Bis(4-fluorophenyl)methyl]-4-[1-(3-fluorophenylcarbamoyl)ethyl]piperazine;

1-69. 1-(4-Chlorobenzhydryl)-4-(4-methoxyphenylcarbamoylmethyl)piperazine;

1-75. 1-(4-Chlorobenzhydryl)-4-(2,4,6-trimethylphenylcarbamoylmethyl)piperazine;

2-7. 1-[Bis(4-fluorophenyl)methyl]-4-[(4-methoxyphenyl)carbamoylmethyl]-2,5-dimethylpiperazine;

2-11. 1-[Bis(4-fluorophenyl)methyl]-4-[(2,4,6-trimethylphenyl)carbamoylmethyl]-3-methylpiperazine;

2-19. 1-[Bis(4-fluorophenyl)methyl]-4-[(3-fluorophenyl)carbamoylmethyl]-3,3-dimethylpiperazine;

7-52. 1-[Bis(4-fluorophenyl)methyl]-4-[1-(1-adamantylcarbamoyl)ethyl]homopiperazine;

and pharmaceutically acceptable salts thereof, especially the hydrochloride and maleate.

The compounds of the present invention can be prepared by reacting a compound of formula (IV):

A—M—H   (IV)

(in which A and M are as defined above) or an active derivative thereof with a compound of formula (V):

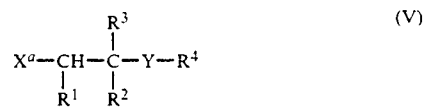

$$X^a-CH-\underset{\underset{R^2}{|}}{\overset{\overset{R^3}{|}}{C}}-Y-R^4 \quad (V)$$
$$\quad\;\; |$$
$$\quad\;\; R^1$$

(in which $R^1$, $R^2$, $R^3$ and $R^4$ are as defined above, and $X^a$ represents a halogen atom, a carboxylic acyloxy group or a sulfonyloxy group).

Where $X^a$ represents a halogen atom, this is preferably a chlorine, bromine or iodine atom. Where $X^a$ represents a carboxylic acyloxy group, this is preferably an aliphatic carboxylic acyloxy group and more preferably a fatty acid acyloxy group, particularly a halogenated acetoxy group, such as a trifluoroacetoxy, chloroacetoxy or trichloroacetoxy group. Where $X^a$ represents a sulfonyloxy group, this is preferably: a lower alkanesulfonyloxy group, such as a methanesulfonyloxy or ethanesulfonyloxy group; a halogenated lower alkanesulfonyloxy group, such as a trifluoromethanesulfonyloxy, trichloromethanesulfonyloxy or pentafluoroethanesulfonyloxy group; or an arylsulfonyloxy group, such as a toluenesulfonyloxy (e.g. p-toluenesulfonyloxy) or benzenesulfonyloxy group.

The reaction of the amino compound of formula (IV) with the substituted alkyl halide of formula (V) may be effected in the presence or absence of a solvent and in the presence or absence of a base.

Where a solvent is employed, its nature is not critical, provided that it has no adverse effect on the reaction, and any solvent conventionally used for reactions of this type may equally be employed here. Examples of suitable solvents include: aromatic hydrocarbons, such as benzene, toluene or xylene; ketones, such as acetone; ethers, such as diethyl ether, dimethoxyethane, diethylene glycol dimethyl ether or tetrahydrofuran; amides, such as dimethylformamide, dimethylacetamide or hexamethylphosphoric triamide; and mixtures of any two or more of these solvents. The most preferred solvents are the ethers and the amides. Equally, where a base is employed, its nature is not critical to the invention, and any base conventionally employed in alkylation reactions of this type may be used in this reaction. Examples of suitable bases include: inorganic bases, such as the alkali metal carbonates (e.g. sodium carbonate or potassium carbonate), the alkali metal bicarbonates (e.g. sodium bicarbonate or potassium bicarbonate) and the alkali metal hydrides (e.g. lithium hydride, sodium hydride or potassium hydride); and organic bases, such as triethylamine, diisopropylethylamine, pyridine, 1,5-diazabicyclo[4,3,0]non-5-ene and 1,8-diazabicyclo[5,4,0]undec-7-ene.

The reaction will take place over a wide range of temperatures, and the precise reaction temperature chosen is not critical to the invention. However, we generally find it convenient to carry out the reaction at a temperature of from $-78°$ C. to $+200°$ C., and more preferably from $0°$ C. to $140°$ C. The time required for the reaction may also vary widely, depending on many factors, notably the reaction temperature, the nature of the starting materials, the presence or absence of the solvent, the nature of the solvent if used, the presence or absence of the base and the nature of the base if used, but a period of from 2 hours to 2 days will normally suffice.

If desired, in the resulting compound of formula (I), where one or both of $R^4$ and $R^5$ represents a hydrogen atom, the compound may be reacted with an appropriate reagent to introduce an alkyl, aryl, aralkyl, aromatic heterocyclic or alkenyl group on the nitrogen atom included in the definition of $-Y-R^4$.

This reaction may be effected by reacting the compound of formula (I) with a compound of formula $R^{4'}-X^a$ or $R^{5'}-X^a$ (in Which $X^a$ is as defined above, and $R^{4'}$ and $R^{5'}$ are independently selected from the group consisting of the alkyl, aryl, aralkyl, aromatic heterocyclic and alkenyl groups included in the definitions of $R^4$ and $R^5$). The reaction may be effected in the presence or absence of a solvent and is preferably effected in the presence of a base.

Where a solvent is employed, its nature is not critical, provided that it has no adverse effect on the reaction, and any solvent conventionally used for reactions of this type may equally be employed here. Examples of suitable solvents include: aromatic hydrocarbons, such as benzene, toluene or xylene; ketones, such as acetone; ethers, such as diethyl ether, dimethoxyethane, diethylene glycol dimethyl ether or tetrahydrofuran; amides, such as dimethylformamide, dimethylacetamide or hexamethylphosphoric triamide; and mixtures of any two or more of these solvents. Of these, the ethers and amides are the preferred solvents.

There is equally no restriction on the nature of the base to be employed, and any base conventionally employed in alkylation and other reactions of this type may be used in this reaction. Examples of suitable bases include: inorganic bases, such as the alkali metal carbonates (e.g. sodium carbonate or potassium carbonate), the alkali metal bicarbonates (e.g. sodium bicarbonate or potassium bicarbonate), the alkali metal hydrides (e.g. lithium hydride, sodium hydride or potassium hydride) and the alkali metal hydroxides (e.g. sodium hydroxide or potassium hydroxide); organic bases, such as triethylamine, diisopropylethylamine, pyridine, 1 5-diazabicyclo[4,3,0]non-5-ene and 1,8-diazabicyclo[5,4,0]undec-7-ene; and basic organic metal compounds, such as butyllithium or lithium diisopropylamide.

The reaction will take place over a wide range of temperatures, and the precise reaction temperature chosen is not critical to the invention. However, we generally find it convenient to carry out the reaction at a temperature of from $-78°$ C. to $+100°$ C., and more preferably from $-10°$ C. to $+30°$ C. The time required for the reaction may also vary widely, depending on many factors, notably the reaction temperature, the nature of the starting materials, the presence or absence of the solvent, the nature of the solvent if used, the presence or absence of the base and the nature of the base if used, but a period of from 2 hours to 2 days will normally suffice.

The compounds of formula (IV) used as the starting materials may be obtained commercially or may be synthesised by the method described in J.A.C.S., 62, 1202 (1940) or in Japanese patent publication No. 46-24024 (1971), or they may be obtained by reduction of a compound thus synthesized.

BIOLOGICAL ACTIVITY

The compounds of the present invention have an excellent blocking effect on the entry of calcium into body cells and can thus offer significant protection against the adverse effects of cellular calcium overload; for example, they offer substantial protection against the lethal effects of low oxygen levels in the blood (especially for the brain) and can, therefore, be used to improve the condition of patients suffering from vascular disorders. Also, they have demonstrated a remarkably low toxicity.

Calcium Entry Blocking Effect

This test was carried out according to the method of J. Booher [Neurobiology, 2, 97-105 (1972)].

The brain was harvested from rats one day after birth and unravelled through a nylon mesh. The unravelled brain cells were incubated in a plastic dish with a diameter of 35 mm, using as culture medium Dulbeccos Modified Eagle Medium (DMEM) containing 20-50% by weight of fetal calf serum. After the cells had been cultivated for 3 weeks, the glial cells were washed with DMEM and then incubated for 90 minutes with DMEM containing 20 μM of A23187 and the test compound. At the end of this time, the liquid medium was removed, and the dead cells were stained with 0.04% Trypan Blue. They were then examined under a microscope to determine the number of dead cells. [Science, 206, 700 (1979), F.A.X. Shanne et al.].

The suppressive rate was calculated as:

$$\frac{N_o - N_t}{N_o}$$

where $N_o$ is the number of cells killed by A23187 alone and $N_t$ is the number of cells killed by A23187 plus the test compound. The results are shown in Table 11. In this Table, as well as in Table 12, the compounds of the invention are identified by the numbers assigned to them in foregoing Tables 1 to 10.

TABLE 11

| Compound No. | Concentration (μg/ml) | Suppressive Rate (%) |
|---|---|---|
| 1-13 | 5 | 79 |
| 1-48 | 5 | 87 |
| 1-75 | 5 | 78 |
| 2-2 | 5 | 81 |
| 2-7 | 5 | 74 |
| Flunarizine | 5 | 53 |
| Cinepazide | 5 | 6 |

Protection Against Lethal Effects Of Low Atmospheric Oxygen Levels

Following an intraperitoneal injection of the test compound to male mice of the ddy strain, aged from 5 to 6 weeks, the mice were placed in a plastic box which was then filled with 96% nitrogen—4% oxygen by volume, to measure the time required until death. As shown in Table 12, the compounds of the present invention were found to prolong the time until death.

TABLE 12

| Compound No. | Dose (mg/kg) | Prolongation Rate (%) |
|---|---|---|
| 1-75 | 30 | 93 |
| Flunarizine | 100 | −29 |
| Cinepazide | 100 | −11 |

It can be seen from the results reported in Tables 11 and 12 that the compounds of the present invention are significantly better than flunarizine and cinepazide as calcium entry blockers and are very substantially better than these prior art compounds at protecting against the lethal effects of low oxygen levels. Accordingly, the compounds of the present invention may be expected to be of considerable value in the treatment of vascular disorders, especially cerebral vascular disorders and most particularly those arising from ischemic effects.

The compounds of the present invention may be administered by any convenient route, as is well known in this field, and the form of pharmaceutical preparation will be chosen having regard to the chosen route of administration. For example, for oral administration, the compounds may be administered in the form of tablets, capsules, granules, powders or syrups. For parenteral administration, they may be formulated as injections or suppositories. These preparations may be produced in a conventional manner using such common additives, adjuvants, diluents and carriers as excipients, binders, disintegrators, lubricants, stabilizers, corrigents and the like. The recommended dosage will, of course, vary depending upon the age and body weight of the patient as well as the nature, symptoms and severity of the disease. However, for an adult human patient, a daily dose of from 1 mg to 100 mg per kg body weight (which may be administered in a single dose or in divided doses) is suggested.

The preparation of various of the compounds of the present invention is further illustrated in the following non-limiting Examples.

EXAMPLE 1

1-[Bis(4-fluorophenyl)methyl]-4-(1-naphthylcarbamoylmethyl)piperazine and its hydrochloride (Compound No. 1-9)

A mixture of 290 mg of 1-[bis(4-fluorophenyl)methyl]piperazine and 400 mg of N-(1-naphthyl)-chloroacetamide was dissolved in 10 ml of a 1:1 by volume mixture of tetrahydrofuran and N,N-dimethylformamide. 1.2 g of anhydrous potassium carbonate were then added to the solution, after which the reaction mixture was stirred for 15 hours at 25° C. and then diluted with ethyl acetate. The organic layer was washed three times with water and then dried over anhydrous magnesium sulfate. The solvent was evaporated off under reduced pressure. The residue was subjected to silica gel thin layer chromatography using a 1:1 by volume mixture of cyclohexane and ethyl acetate as the developing solvent, to afford 430 mg of 1-[bis(4-fluorophenyl)methyl]4-(1-naphthylcarbamoylmethyl)-piperazine, melting at 173° C.

Nuclear Magnetic Resonance Spectrum (60 MHz, CDCl$_3$) δ ppm:
2.3–2.9 (8H);
3.25 (2H, singlet);
4.30 (1H, singlet);
6.8–8.4 (15H);
9.95 (1H, singlet).

Infrared Absorption Spectrum (liquid) $v_{max}$ cm$^{-1}$: 3270, 1690, 1600.

Mass Spectrum (m/e): 471, 301, 203.

300 mg of this compound Were dissolved in 5 ml of acetone, and then a 4.92M ethanolic solution of hydrogen chloride were added dropwise, to precipitate 310 mg of the title dihydrochloride, melting at 165°–172° C.

Elemental analysis:
Calculated for C$_{29}$H$_{27}$N$_3$OF$_2$.2HCl:
C, 63.97%; H, 5.37%; N, 7.72%.
Found; C, 63.75%; H, 5.40%; N, 7.75%.

Nuclear Magnetic Resonance Spectrum (270 MHz, CD$_3$OD) δ ppm:
3.18–3.29 (4H);
3.68–3.80 (4H);
4.43 (2H, singlet);
5.23 (1H, singlet);
7.1–8.1 (15H).

EXAMPLE 2

1-(4-Chlorobenzhydryl)-4-(2,4,6-trimethylphenylcarbamoylmethyl) piperazine hydrochloride (Compound No. 1-75)

2 g of anhydrous potassium carbonate were added to a mixture of 192.6 mg of 1-(4-chlorobenzhydryl)piperazine and 142.7 mg of N-(2,4,6-trimethylphenyl)-chloroacetamide dissolved in 20 ml of N,N-dimethylformamide, and the reaction mixture was stirred at 80° C. for 7.5 hours. At the end of this time, ethyl acetate was added to the mixture, and the organic layer was separated. The organic layer was washed three times with water, and then the solvent was evaporated off under reduced pressure. The residue was subjected to silica gel thin layer chromatography using a 1:1 by volume mixture of cyclohexane and ethyl acetate as the developing solvent, to afford a purified 1-(4-chlorobenzhydryl)-4-(2,4,6-trimethylphenylcarbamoylmethyl)piperazine.

Infrared Absorption Spectrum (liquid) $v_{max}$ cm$^{-1}$: 3280, 2910, 2810, 1715, 1700, 1610, 1600, 1510.

Nuclear Magnetic Resonance Spectrum (60 MHz, CDCl$_3$) δ ppm:
2.10 (6H, singlet);
2.21 (3H, singlet);
1.9–2.9 (8H, multiplet);
3.12 (2H, singlet);
4.21 (1H, singlet);
7.1–7.7 (9H, multiplet);
8.56 (1H, broad singlet).

Mass Spectrum (m/e): 461, 201.

This purified 1-(4-chlorobenzhydryl)-4-(2,4,6-trimethylphenylcarbamoylmethyl)piperazine was dissolved in 5 ml of ethanol and mixed with an excess of a 4.92M ethanolic solution of hydrogen chloride. The resulting hydrochloride was crystallized by addition of diethyl ether, to afford 207.3 mg of the crude dihydrochloride of the title compound as crystals, melting at 40°–145° C.

This compound was recrystallized from a mixture of ethanol and diethyl ether, to give the monohydrate of the title compound, melting at 149.5°–150.5° C.

Elemental Analysis:
Calculated for C$_{28}$H$_{32}$N$_3$O$_2$Cl.2HCl.H$_2$O:
C, 60.82%; H, 6.56%; N, 7.60%.
Found: C, 61.32%; H. 6.82%; N, 7.53%.

Nuclear Magnetic Resonance Spectrum (270MHz, CD$_3$OD) δ ppm:
2.16 (6H. singlet);
2.25 (3H, singlet);
3.30 (4H, broad singlet);
3.65 (4H, broad singlet);
4.35 (2H, singlet);
5.30 (1H, singlet);
6.90 (2H, singlet);
7.3–7.9 (9H, multiplet).

EXAMPLE 3

1-[Bis(4-fluorophenyl)methyl-4-[(2,4,6-trimethylphenyl)carbamoylmethyl]-3-methypiperazine hydrochloride (Compound No. 2-11)

A mixture of 300 mg of 1-[bis(4-fluorophenyl)methyl]-3-methylpiperazine and 252 mg of N-(2,4,6-trimethylphenyl) chloroacetamide was dissolved in 20 ml of a 1:1 by volume mixture of tetrahydrofuran and N,N-dimethylformamide. 100 mg of anhydrous potassium carbonate were then added to the solution, and the reaction mixture was stirred at 70° C. for 3 hours, after which ethyl acetate was added to it and the organic layer was separated. The organic layer was washed three times with water, and then dried over anhydrous magnesium sulfate. The solvent was then removed by evaporation under reduced pressure, and the residue was subjected to silica gel thin layer chromatography using a 1:1 by volume mixture of cyclohexane and ethyl acetate as the developing solvent, to afford a purified 1-[bis(4-fluorophenyl)methyl]-4-[(2,4,6-trimethylphenyl)carbamoylmethyl]-3-methylpiperazine.

Infrared Absorption (liquid) $v_{max}$ cm$^{-1}$: 3275, 1680, 1600, 1500, 1220, 1150, 1040.

Nuclear Magnetic Resonance Spectrum (60 MHz, CDCl$_3$) δ ppm:
1.08 (3H, doublet, J=6 Hz);
2.14 (6H, singlet);
2.22 (3H, singlet);
1.55–2.95 (7H, multiplet);
2.85 (1H, doublet, J=18 Hz);

3.52 (1H, doublet, J=18 Hz);
4.18 (1H, singlet);
6.65-7.55 (10H, multiplet).
Mass Spectrum (m/e): 477, 203.

This purified 1-[bis(4-fluorophenyl)methyl]-4-[(2,4,6-trimethylphenyl)carbamoylmethyl]-3-methylpiperazine was dissolved in 3 ml of ethanol, and the resulting solution was mixed with an excess of a 4.92M ethanolic solution of hydrogen chloride. Diethyl ether was then added, to afford 255 mg of the crystalline title dihydrochloride.

EXAMPLE 4

1-[Bis(4-fluorophenyl)methyl]-4-[(4-methoxyphenyl)-carbamoylmethyl]-2,5-dimethylpiperazine hydrochloride (Compound No. 2-7)

A mixture of 416 mg of 1-[bis(4-fluorophenyl)methyl]-2,5-dimethylpiperazine and 316 mg of N-(4-methoxyphenyl)chloroacetamide was dissolved in 5 ml of a 1:1 by volume mixture of tetrahydrofuran and N,N-dimethylformamide. 365 mg of anhydrous potassium carbonate were then added to the solution, and the reaction mixture was stirred at 80° C. for 5 hours. At the end of this time, ethyl acetate was added to the mixture, and the organic layer was separated. The organic layer was washed three times with water, and then dried over anhydrous magnesium sulfate. The solvent was removed by evaporation under reduced pressure, and the residue was subjected to silica gel thin layer chromatography using a 2:1 by volume mixture of cyclohexane and ethyl acetate as the developing solvent, to afford a purified 1-[bis(4-fluorophenyl)methyl]-4-[(4-methoxyphenyl) carbamoylmethyl]-2,5-dimethylpiperazine, melting at 131° C.

Elemental analysis:
Calculated for $C_{28}H_{31}N_3O_2$:
C, 70.13%; H, 6.52%; N, 8.76%.
Found: C, 69.93%; H, 6.53%; N, 8.78%.

Infrared Absorption Spectrum (chloroform) $v_{max}$ cm$^{-1}$:
3350, 1670, 1520, 1505, 1245.

Nuclear Magnetic Resonance Spectrum (60 MHz, CDCl$_3$) δ ppm:
1.04 (3H, doublet, J=6 Hz);
1.18 (3H, doublet, J=6 Hz);
1.8-2.93 (6H, multiplet);
3.12 (2H, doublet, J=18 Hz);
3.76 (3H, singlet);
5.50 (1H, singlet);
6.78-7.52 (12H, multiplet);
9.07 (1H, broad singlet).

This purified 1-[bis(4-fluorophenyl)methyl]-4-[(4-methoxyphenyl)carbamoylmethyl]-2,5-dimethylpiperazine was dissolved in 30 ml of diethyl ether. An excess of a 4.92M ethanolic solution of hydrogen chloride was added to the solution to yield a white precipitate, which was collected by filtration, to afford 532 mg of the monohydrate of the title compound, melting at 141° C.

Elemental Analysis:
Calculated for $C_{28}H_{31}N_3O_2F_2.2HCl.H_2O$:
C, 58.95%; H, 5.83%; N, 7.36%.
Found: C, 58.41%; H, 6.21%; N, 7.32%.

1 g of this compound was recrystallized by dissolving it in 5 ml of ethanol and then adding 5 ml of diethyl ether, to give 950 mg of the corresponding anhydride, melting at 160°-170° C.

Elemental Analysis:
Calculated for $C_{28}H_{31}N_3O_2F_2.2HCl$:
C, 60.87%; H, 6.02%; N, 7.61%.
Found: C, 60.49%; H, 6.07%; N, 7.47%.

Nuclear Magnetic Resonance Spectrum (270 MHz, CD$_3$OD) δ ppm:
1.36 (3H, doublet, J=6.2 Hz);
1.43 (3H, doublet, J=5.9 Hz);
3.15-4.30 (6H, multiplet);
4.09 (2H, doublet, J=15.8 Hz);
3.76 (3H, singlet);
5.88 (1H, singlet);
6.86-7.69 (12H, multiplet).

Infrared Absorption Spectrum (Nujol - trade mark) $v_{max}$ cm$^{-1}$:
3410, 1696, 1609, 1512, 1417.

Ultraviolet Absorption Spectrum (ethanol) $\lambda_{max}$:
253 nm (ε=17,800).

EXAMPLE 5

1-[Bis(4-fluorophenyl)methyl]-4-(3-fluorophenylcarbamoylmethyl)piperazine hydrochloride or maleate (Compound No. 1-13)

A mixture of 300 mg of 1-[bis(4-fluorophenyl)methyl]piperazine and 234 mg of N-(3-fluorophenyl)-chloroacetamide was dissolved in 20 ml of a 1:1 by volume mixture of tetrahydrofuran and N,N-dimethylformamide, and 400 mg of anhydrous potassium carbonate were added to the solution. The reaction mixture was then stirred at 70° C. for 2 hours, after which ethyl acetate was added to it and the organic layer was separated. The organic layer was washed three times with water, and then dried over anhydrous magnesium sulfate. The solvent was removed by evaporation under reduced pressure. The residue was subjected to silica gel thin layer chromatography using a 2:1 by volume mixture of cyclohexane and ethyl acetate as the developing solvent, to give a purified 1-[bis(4-fluorophenyl)methyl]-4-(3-fluorophenylcarbamoylmethyl)piperazine.

Nuclear Magnetic Resonance Spectrum (60 MHz, CDCl$_3$) δ ppm:
2.18-3.88 (8H, multiplet);
3.1 (2H, singlet);
4.22 (1H, singlet);
6.58-7.78 (12H multiplet);
9.23 (1H, singlet). Infrared Absorption Spectrum (liquid) $v_{max}$ cm$^{-1}$:
3300, 1680, 1600, 1520, 1440, 1330, 1220.

Mass Spectrum (m/e): 437, 203.

The whole of the 1-[bis(4-fluorophenyl)methyl]-4-(3-fluorophenylcarbamoylmethyl)piperazine obtained as described above was then dissolved in 3 ml of ethanol. An excess of a 4.92M ethanolic solution of hydrogen chloride was added to the solution, after which the resulting compound was crystallized by adding diethyl ether, to afford 244 mg of the title hydrochloride, melting at 145°-154° C.

Nuclear Resonance Spectrum (270 MHz, CD$_3$OD) δ ppm:
3.47 (4H, broad singlet);
3.88 (4H, broad singlet);
4.32 (2H, singlet);
5.60 (1H, singlet);
6.8-7.9 (12 H).

The purified 1-[bis(4-fluorophenyl)methyl]-4-(3-fluorophenylcarbamoylmethyl)piperazine obtained as described above was also dissolved in 3 ml of ethanol, and then an ethanolic solution containing one molar equivalent of maleic acid was added. The resulting product was crystallized by adding diethyl ether, to afford the maleate.

Nuclear Magnetic Resonance Spectrum (270 MHz, CD$_3$OD) δ ppm:
2.72 (4H);
3.35 (4H);
3.99 (2H, singlet);
4.52 (1H, singlet);
6.26 (2H, singlet);
6.8–6.9 (1H, multiplet);
7.0–7.2 (4H, multiplet);
7.2–7.4 (2H, multiplet);
7.4–7.6 (5H, multiplet).

EXAMPLE 6

1-[Bis(4-fluorophenyl)methyl]-4-[1-(1-adamantylcarbamoyl)ethyl]homopiperazine maleate (Compound No. 7-52)

A mixture of 300 mg of 1-[bis(4-fluorophenyl) methyl]homopiperazine and 300 mg of N-(1-adamantyl)-2-bromopropionamide Was dissolved in 20 ml of a 1:1 by volume mixture of tetrahydrofuran and N,N-dimethylformamide, and then 100 mg of anhydrous potassium carbonate were added to the resulting solution. The reaction mixture was stirred at 90° C. for hours, and then ethyl acetate was added, and the organic layer was separated. The organic layer was washed three times with water, and then dried over anhydrous magnesium sulfate. The solvent was removed by evaporation under reduced pressure, and the residue was subjected to silica gel thin layer chromatography using a 1:1 by volume mixture of cyclo hexane and ethyl acetate as the developing solvent, to give a purified 1-[bis(4-fluorophenyl)methyl]-4-[1-(1-adamantylcarbamoyl)ethyl]homopiperazine.

Nuclear Magnetic Resonance Spectrum (60 MHz, CDCl$_3$) δ ppm:
1.15 (3H, doublet, J=7 Hz);
1.45–2.3 (17H, multiplet);
2.4–2.9 (8H, multiplet);
3.15 (1H, quartet, J=7 Hz);
4.6 (1H, singlet);
6.8–7.6 (8H, multiplet).

Infrared Absorption Spectrum (liquid) $\nu_{max}$ cm$^{-1}$: 3350, 1740, 1660, 1600, 1510, 1450, 1360, 1220.

Mass Spectrum (m/e): 507, 329, 203.

This purified product was dissolved in acetone, and the solution was mixed with 0.5 mole of maleic acid. The resulting salt was crystallized by adding diethyl ether to afford 100 mg of the title compound.

EXAMPLE 7

1-Bis(4-fluorophenyl)methyl]-4-[1-(3-fluorophenylcarbamoyl)ethyl]piperazine hydrochloride (Compound No. 1-44)

A mixture of 300 mg of 1-[bis(4-fluorophenyl)methyl]piperazine and 256 mg of N-(3-fluorophenyl) -2-bromopropionamide was dissolved in 20 ml of a 1:1 by volume mixture of tetrahydrofuran and N,N-dimethylformamide, and 100 mg of anhydrous potassium carbonate were added to the resulting solution. The reaction mixture was then stirred at 90° C. for 2 hours. At the end of this time, ethyl acetate was added, and the organic layer was separated. The organic layer was washed three times with water, and then dried over anhydrous magnesium sulfate. The solvent was removed by evaporation under reduced pressure, and the residue was subjected to silica gel thin layer chromatography using a 1:1 by volume mixture of cyclohexane and ethyl acetate as the developing solvent, to give 1-[bis(4-fluorophenyl)methyl]-4-[1-(3-fluorophenylcarbamoyl)ethyl]piperazine.

Infrared Absorption Spectrum (liquid) $\nu_{max}$ cm$^{-1}$: 3300, 1700, 1600, 1510, 1440, 1220, 1140.

Nuclear Magnetic Resonance Spectrum (60 MHz, CDCl$_3$) δ ppm:
1.28 (3H, doublet, J=7 Hz);
2.1–2.9 (8H, multiplet);
3.15 (1H, quartet, J=7 Hz): 4.22 (1H, singlet); 6.5–7.5 (12H, multiplet); 9.4 (1H, singlet).

Mass Spectrum (m/e): 453, 203.

The product obtained as described above was dissolved in 3 ml of ethanol, and an excess of a 4.92M ethanolic solution of hydrogen chloride was added to the solution. The resulting hydrochloride was then crystallized by adding diethyl ether. to afford 250 mg of the title compound.

EXAMPLE 8

1-Bis(4-fluorophenyl)methyl]-4-[1-(1,2,3,4-tetrahydroquinoline-1-carbonyl)ethyl]piperazine hydrochloride (Compound No. 1-37)

A mixture of 300 mg of 1-[bis(4-fluorophenyl)methyl]piperazine and 280 mg of N-(1,2,3,4-tetrahydro-1-quinolyl)-2-bromopropionamide was dissolved in 20 ml of a 1:1 by volume mixture of tetrahydrofuran and N,N-dimethylformamide, and 100 mg of anhydrous potassium carbonate were added to the resulting solution. The solution was then stirred at 90° C. for 2 hours, after which ethyl acetate was added, and the organic layer was separated. The organic layer was washed three times with water, and dried over anhydrous magnesium sulfate. The solvent was then removed by evaporation under reduced pressure, and the resulting residue was subjected to silica gel thin layer chromatography using a 1:1 by volume mixture of cyclohexane and ethyl acetate as the developing solvent, to give a purified 1-[bis(4-fluorophenyl)methyl]-4-[1-(1,2,3,4-tetrahydroquinoline-1-carbonyl)ethyl]piperazine.

Infrared Absorption Spectrum (liquid) $\nu_{max}$ cm$^{-1}$: 1730, 1640, 1575, 1500.

Nuclear Magnetic Resonance Spectrum (60 MHz, CDCl$_3$) δ ppm;
1.23 (3H, doublet, J=7 Hz):
1.6–2.8 (12H, multiplet);
3.6–4.02 (4H, multiplet);
4.19 (1H, singlet);
6.8–7.48 (12H, multiplet).

Mass Spectrum (m/e): 475, 203.

The purified product obtained as described above was dissolved in 3 ml of ethanol, and an excess of a 4.92M ethanolic solution of hydrogen chloride was added to the solution. The hydrochloride was crystallized by adding diethyl ether, to yield 265 mg of the title compound as the dihydrochloride.

EXAMPLE 9

1-Bis(4-fluorophenyl)methyl]-4-[(3-fluorophenyl)carbamoylmethyl]-3,3-dimethylpiperazine hydrochloride (Compound No. 2-19)

A mixture of 283 mg of 1-[bis(4-fluorophenyl)methyl]-3,3-dimethylpiperazine and 204 mg of N-(3-fluorophenyl)chloroacetamide was dissolved in 20 ml of a 1:1 by volume mixture of tetrahydrofuran and N,N-dimethylformamide, and 1 g of anhydrous potassium carbonate was added to the resulting solution. The reaction mixture was then stirred at 80° C. for 16 hours, after which ethyl acetate was added, and the organic layer was separated. The organic layer was washed with water and dried over anhydrous magnesium sulfate. The solvent was then removed by evaporation under reduced pressure. The residue was subjected to silica gel thin layer chromatography using a 2:1 by volume mixture of cyclohexane and ethyl acetate as the developing solvent, to give a purified 1-[bis(4-fluorophenyl)methyl]-4-[(3-fluorophenyl)carbamoylmethyl]-3,3-dimethylpiperazine.

Infrared Absorption Spectrum (chloroform) $\nu_{max}$ cm$^{-1}$:
3270, 2910, 1690, 1600, 1505.

Nuclear Magnetic Resonance Spectrum (60 MHz, CDCl$_3$) δ ppm:
1.08 (6H, singlet);
2.0–2.9 (6H, multiplet);
3.10 (2H, singlet);
4.19 (1H, broad singlet);
8 (12H, multiplet);
6.5–7.8 (12H, multiplet);
9.54 (1H, broad singlet).

Mass Spectrum (m/e): 467, 203.

The purified product was dissolved in 30 ml of diethyl ether, and an excess of a 4.92M ethanolic solution of hydrogen chloride was added to the solution. The resulting white precipitate was collected by filtration to afford 49.8 mg of the title compound dihydrochloride.

EXAMPLE 10

1-[Bis(4-fluorophenyl)methyl]-4-[2-(3-fluorophenylamino)ethyl]piperazine and its hydrochloride (Compound No. 5-9)

160 mg of 1-[bis(4-fluorophenyl)methyl]-4-(3-fluorophenylcarbamoylmethyl)piperazine (prepared as described in Example 5) were dissolved in 10 ml of anhydrous tetrahydrofuran, and 300 mg (a large excess) of lithium aluminum hydride were added to the solution. The mixture was then heated under reflux for 8 hours and cooled, after which the remaining lithium aluminum hydride was reacted with small amount of a saturated aqueous solution of sodium sulfate, and tetrahydrofuran was added. The resulting white precipitate was removed by filtration, and then the solvent was removed by evaporation under reduced pressure. The resulting crude product was subjected to silica gel thin layer chromatography using a 1:1 by volume mixture of cyclohexane and ethyl acetate as the developing solvent, to afford 84 mg of the title compound (the free base).

Infrared Absorption Spectrum (liquid) $\nu_{max}$ cm$^{-1}$:
3450.

Nuclear Magnetic Resonance Spectrum (60 MHz, CDCl$_3$)
~2.42 (1H, broad singlet);
2.3–2.7 (4H, multiplet);
2.9–3.3 (4H, singlet);
4.2 (1H, singlet);
6.1–7.5 (12H, multiplet).

Spectrum (m/e): 425, 203.

The free base obtained as described above was dissolved in acetone, and an excess of a 4.92M ethanolic solution of hydrogen chloride was added to the solution. The white precipitate thus obtained was collected by filtration and washed with diethyl ether, to afford 85 mg of the title compound trihydrochloride.

EXAMPLE 11

1-Bis(4-fluorophenyl)methyl]-4-[N-allyl-N-(3-fluorophenyl)carbamoylmethyl]piperazine hydrochloride (Compound No. 1-27)

12.65 mg of sodium hydride were added at room temperature to a solution of 115 mg of 1-[bis(4fluorophenyl)methyl]-4-(3-fluorophenylcarbamoylmethyl)piperazine (prepared as described in Example 5) in 10 ml of a 1:1 by volume mixture of tetrahydrofuran and N,N-dimethylformamide, whilst stirring, over a period of 20 minutes. 31.6 mg of allyl bromide were then added to the reaction mixture, after which the mixture was stirred overnight and then mixed with ethyl acetate. It was then washed three times with water, and dried over anhydrous magnesium sulfate. The solvent was then removed by evaporation under reduced pressure, and the resulting residue was subjected to silica gel thin layer chromatography using a 1:1 by volume mixture of cyclohexane and ethyl acetate as the developing solvent, to give 40 mg of a purified 1-[bis(4-fluorophenyl)methyl]-4-[N-allyl-N-(3-fluorophenyl)carbamoylmethyl]piperazine.

Infrared Absorption Spectrum (liquid) $\nu_{max}$ cm$^{-1}$:
1730, 1660, 1500, 1460.

Nuclear Magnetic Resonance Spectrum (60 MHz, CDCl$_3$) δ ppm:
2.1–2.7 (8H, multiplet);
2.91 (2H, singlet);
4.18 (2H, singlet);
4.29 (1H, singlet);
4.8–6.15 (3H, multiplet);
6.7–7.5 (12H, multiplet).

Mass Spectrum (m/e): 479, 203.

The purified product was dissolved in ethanol, and an excess of a 4.92M ethanolic solution of hydrogen chloride was added to the solution. The resulting hydrochloride was crystallized by adding diethyl ether, to afford 27 mg of the title compound.

EXAMPLE 12

1-[Bis(4-fluorophenyl)methyl]-4-[(4-methoxyphenyl)carbamoylmethyl]-2,5-(trans)dimethylpinerazine hydrochloride A mixture of 5 g of 1-bis(4-fluorophenyl)methyl alcohol in 10 ml of concentrated hydrochloric acid was heated under reflux for 4 hours. At the end of this time, the reaction mixture was separated into two phases in situ, and the organic layer was distilled under reduced pressure [130°–133° C./1.5 mmHg (~200 Pa)], to give 4.26 g of colorless 1-bis(4-fluorophenyl)methyl chloride. A mixture of the whole of this 1-bis(4-fluorophenyl)methyl chloride and 4.08 g (2 molar equivalents) of 2,5-(trans)dimethylpiperazine in 85 ml of toluene was then heated under reflux for 9 hours. At the end of this time. the reaction mixture was extracted with 2.6M aqueous acetic acid, and the extract was adjusted to a basic pH by the addition of aqueous ammonia and extracted with ethyl acetate. The extract was washed with a saturated aqueous solution of sodium chloride and dried over anhydrous magnesium sulfate. The solvent was then removed by distillation under reduced pressure. The residue was purified by silica gel column chromatography, using a 10:1 by volume mixture of ethyl acetate and methanol as eluent, to give 3.96 g of 1-[bis(4-fluorophenyl)methyl]-2,5-(trans)dimethylpiperazine, as crystals melting at 98° C.

Elemental analysis:
Calculated for $C_{19}H_{22}N_2F_2$:
C, 72.13%; H, 7.09%; N, 8.85%.
Found: C, 71.93%; H, 7.09%; N, 8.83%.

Nuclear Magnetic Resonance Spectrum (60 MHz, $CDCl_3$) δ ppm:
0.93 (3H, doublet, J=6 Hz);
1.15 (3H, doublet, J=6 Hz);
2.12–3.02 (6H, multiplet);
5.33 (1H, singlet);
6.83–7.52 (8H, multiplet).

Infrared Absorption Spectrum (KBr) $v_{max}$ cm$^{-1}$: 0, 1600, 1504, 1222, 1150.

This was then treated as described in Example 4, to give the title compound having essentially the same properties as the product of Example 4.

EXAMPLES 13 TO 95

The following compounds were also prepared using procedures similar to those described above in Examples 1to 12. In the following description, the compounds of the present invention are identified by the numbers heretofore assigned to them in Tables 1 to 10:

Compound No. 1-1

Nuclear Magnetic Resonance Spectrum (60 MHz, $CDCl_3$)
1.4–2.2 (4H, multiplet):
2.2–2.8 (8H, multiplet):
3.1 (2H, singlet);
3.2–3.8 (4H, multiplet);
4.25 (1H, singlet); 6.8–7.5 (8H, multiplet).
Mass Spectrum (m/e): 399, 203.

Compound No. 1-2

Infrared Absorption Spectrum (liquid) $v_{max}$ cm$^{-1}$: 1650, 1600, 1500, 1400, 1220, 1150, 1010.
Nuclear Magnetic Resonance Spectrum (60 MHz, $CDCl_3$) δ ppm:
1.6–2.9 (12H, multiplet);
3.29 (2H, singlet);
3.75 (2H, triplet, J=6 Hz);
4.2 (1H, singlet);
6.7–7.7 (12H, multiplet).
Mass Spectrum (m/e): 461, 203.

Compound No. 1-3

Infrared Absorption Spectrum (liquid) $v_{max}$ cm$^{-1}$: 1740, 1640, 1500, 1220, 1160.
Nuclear Magnetic Resonance Spectrum (60 MHz, $CDCl_3$) δ ppm:
0.7–3.7 (28H, multiplet);
4.6 (1H, singlet);
6.7–7.6 (8H, multiplet).
Mass Spectrum (m/e): 481, 203.

Compound No. 1-4

Infrared Absorption Spectrum (liquid) $v_{max}$ cm$^{-1}$: 1690.
Nuclear Magnetic Resonance Spectrum (60 MHz, $CDCl_3$) δ ppm:
2.2–2.8 (8H, multiplet);
3.1 (2H, singlet);
3.75 (6H, singlet);
4.25 (1H, singlet);
6.15–7.50 (11H, multiplet).
Mass Spectrum (m/e): 481, 203.

Compound No. 1-5

Infrared Absorption Spectrum (liquid) $v_{max}$ cm$^{-1}$: 3320, 1680, 1600, 1510, 1410, 1300, 1220.
Nuclear Magnetic Resonance Spectrum (60 MHz, $CDCl_3$) δ ppm:
2.2–2.9 (8H, multiplet);
3.1 (2H, singlet);
3.72 (3H, singlet);
4.23 (1H, singlet);
6.7–7.6 (12H, multiplet);
8.94 (1H, singlet).
Mass Spectrum (m/e): 451, 301, 203.

Compound No. 1-6

Infrared Absorption Spectrum (liquid) $v_{max}$ cm$^{-1}$: 3400, 1680, 1600, 1510, 1300, 1220, 1160, 1016.
Nuclear Magnetic Resonance Spectrum (60 MHz, $CDCl_3$) δ ppm:
0.9 (6H, doublet, J=6 Hz);
1.3–2.0 (1H, multiplet);
2.2–2.8 (8H, multiplet);
3.0 (2H, singlet); 3.1 (2H, triplet, J=6 Hz); 4.21 (1H, singlet); 6.8–7.6 (8H, multiplet).
Mass Spectrum (m/e): 401, 301, 203.

Compound No. 1-7

Infrared Absorption Spectrum (liquid) $v_{max}$ cm$^{-1}$: 400, 1680, 1600, 1500, 1450, 1410, 1220, 1130.
Nuclear Magnetic Resonance Spectrum (60 MHz, $CDCl_3$) δ ppm:
2.3–2.8 (8H, multiplet);
3.1 (2H, singlet);
3.8 (3H, singlet);
3.85 (6H, singlet);
4.29 (1H, singlet);
6.8–7.5 (10H, multiplet);
9.03 (1H, singlet).
Mass Spectrum (m/e): 511, 301, 203.

Compound No. 1-8

Infrared Absorption Spectrum (liquid) $v_{max}$ cm$^{-1}$: 300, 1650, 1600, 1490, 1440, 1205, 1140.
Nuclear Magnetic Resonance Spectrum (60 MHz, $CDCl_3$) δ ppm:
2.2–2.7 (8H, multiplet);
3.05 (2H, singlet);
4.2 (1H, singlet);
4.46 (2H, doublet, J=5 Hz);
6.7–7.5 (13H, multiplet).
Mass Spectrum (m/e): 435, 301, 203.

Compound No. 1-10

Infrared Absorption Spectrum (liquid) $v_{max}$ cm$^{-1}$: 3350, 1670, 1600, 1500, 1220, 1150, 1010.
Nuclear Magnetic Resonance Spectrum (60 MHz, $CDCl_3$) δ ppm:
0.6–2.1 (11H, multiplet);
2.2–2.8 (8H, multiplet);
3.0 (2H, singlet);
4.25 (1H, singlet);
6.8–7.6 (8H, multiplet).
Mass Spectrum (m/e): 427, 203.

Compound No. 1-11

Infrared Absorption Spectrum (liquid) $v_{max}$ cm$^{-1}$:

3325, 1680, 1600, 1500, 1300, 1220, 1010.
Nuclear Magnetic Resonance Spectrum (60 MHz, CDCl$_3$) δ ppm:
 1.16 (6H, singlet);
 1.23 (3H, singler);
 1.9–2.8 (8H, multiplet);
 3.16 (2H, singlet);
 4.26 (1H, singlet);
 6.8–7.6 (10H, multiplet);
 8.56 (1H, singlet).
Mass Spectrum (m/e): 463, 203.

Compound No. 1-12

Infrared Absorption Spectrum (liquid) ν$_{max}$ cm$^{-1}$:
3350, 1670, 1600, 1500, 1220, 1010.
Nuclear Magnetic Resonance Spectrum (60 MHz, CDCl$_3$) δ ppm:
 1.66 (6H, singlet);
 2.15–2.8 (8H, multiplet);
 2.93 (2H, singlet);
 4.2 (1H, singlet);
 6.75–7.6 (13H, multiplet).
Mass Spectrum (m/e): 463, 301.

Compound No. 1-14

Infrared Absorption Spectrum (liquid) ν$_{max}$ cm$^{-1}$:
300, 1700, 1620, 1600, 1520, 1450, 1220, 1150, 1010.
Nuclear Magnetic Resonance Spectrum (60 MHz, CDCl$_3$) δ ppm:
 2.15–2.85 (8H, multiplet);
 3.14 (2H, singlet);
 4.23 (1H, singlet);
 6.75–7.55 (11H, multiplet);
 8.2–8.65 (1H, multiplet);
 9.55 (1H, singlet).
Mass Spectrum (m/e): 439, 203.

Compound No. 1-15

Infrared Absorption Spectrum (liquid) ν$_{max}$ cm$^{-1}$:
300, 1690, 1600, 1510, 1420, 1220, 1160.
Nuclear Magnetic Resonance Spectrum (60 MHz, CDCl$_3$) δ ppm:
 1.0 (3H, triplet, J=7 Hz);
 1.4–2.1 (2H, multiplet);
 2.2–2.9 (8H, multiplet);
 3.1 (2H, singlet); 3.95 (2H, triplet, J=6 Hz); 4.24 (1H, singlet); 6.7–7.6 (12H, multiplet); 8.91 (1H, singlet).
Mass Spectrum (m/e): 479, 203.

Compound No. 1-16

Infrared Absorption Spectrum (liquid) ν$_{max}$ cm$^{-1}$:
3375, 1745, 1680, 1600, 1500, 1370, 1300, 1220.
Nuclear Magnetic Resonance Spectrum (60 MHz, CDCl$_3$) δ ppm:
 1.21 (3H, triplet, J=7 Hz);
 2.2–2.8 (8H, multiplet);
 3.01 (2H, singlet);
 0 (2H, doublet, J=5 Hz);
 4.15 (2H, quartet, J=7 Hz);
 4.2 (1H, singlet);
 6.75–7.8 (9H, multiplet).
Mass Spectrum (m/e): 431, 203.

Compound No. 1-17:

Infrared Absorption Spectrum (liquid) ν$_{max}$ cm$^{-1}$ 325, 1670, 1600, 1500, 1470, 1380, 1220.
Nuclear Magnetic Resonance Spectrum (60 MHz, CDCl$_3$) δ ppm:
 1.5–1.8 (6H, multiplet);
 1.8–2.2 (9H, multiplet);
 2.2–2.7 (8H, multiplet);
 2.82 (2H, singlet);
 4.15 (1H, singlet);
 6.75–7.6 (8H, multiplet).
Mass Spectrum (m/e): 493, 290.

Compound No. 1-18;

Infrared Absorption Spectrum (liquid) ν$_{max}$ cm$^{-1}$:
3300, 1680, 1600, 1510, 1450, 1160, 1040.
Nuclear Magnetic Resonance Spectrum (60 MHz, CDCl$_3$) δ ppm:
 2.2–2.9 (8H, mutltiplet);
 3.1 (2H, singlet);
 4.26 (1H, singlet):
 5.9 (2H, singlet);
 6.7–7.7 (11H, multiplet);
 9.01 (1H, singlet).
Mass Spectrum (m/e): 465.

Compound No. 1-19:

Infrared Absorption Spectrum (liquid) ν$_{max}$ cm$^{-1}$:
3350, 1660, 1600, 1500, 1300, 1220, 1150, 1010.
Nuclear Magnetic Resonance Spectrum (60 MHz, CDCl$_3$) δ ppm:
 1.5–2.1 (15H, multiplet);
 2.2–2.8 (8H, multiplet);
 3.03 (2H, singlet);
 6.8–7.6 (8H, multiplet).
Mass Spectrum (m/e): 479.

Compound No. 1-20:

Infrared Absorption Spectrum (liquid) ν$_{max}$ cm$^{-1}$:
3300, 1680, 1600, 1510, 1410, 1300, 1210.
Nuclear Magnetic Resonance Spectrum (60 MHz, CDCl$_3$) δ ppm:
 2.2–2.9 (8H, multiplet);
 3.1 (2H, singlet);
 4.27 (1H, singlet);
 6.8–7.8 (12H, multiplet);
 9.14 (1H, singlet).

Compound No. 1-21

Infrared Absorption Spectrum (liquid) ν$_{max}$ cm$^{-1}$:
300, 2840, 1700, 1625, 1605, 1530, 1505.
Nuclear Magnetic Resonance Spectrum (60 MHz, CDCl$_3$) δ ppm:
 2.2–2.9 (8H, multiplet);
 3.10 (2H, singlet);
 4.26 (1H, singlet);
 6.2–7.6 (11H, multiplet);
 9.28 (1H, broad singlet).
Mass Spectrum (m/e): 457, 203.

Compound No. 1-26

Infrared Absorption Spectrum (liquid) ν$_{max}$ cm$^{-1}$:
3300, 1700, 1600, 1510, 1460, 1220, 1160, 1050.
Nuclear Magnetic Resonance Spectrum (60 MHz, CDCl$_3$) δ ppm:
 2.2–2.9 (8H, multiplet):
 3.18 (2H, singlet):
 4.22 (1H, singlet);
 6.7–7.6 (8H, multiplet):
 8.7 (1H, singlet).
Mass Spectrum (m/e): 457, 203.

Compound No. 1-36

Infrared Absorption Spectrum (liquid) $v_{max}$ cm$^{-1}$:
650, 1600, 1500, 1440, 1230, 1160, 1020, 830.
Nuclear Magnetic Resonance Spectrum (60 MHz, CDCl$_3$) δ ppm:
1.25 (3H, doublet, J=6 Hz);
2.1–2.9 (8, multiplet);
3.47 (1H, quartet, J=6 Hz);
4.19 (1H, singlet);
4.7 (1H, doublet, J=14 Hz);
4.78 (2H, singlet);
5.21 (1H, doublet, J=14 Hz);
6.7–7.6 (12H, multiplet).
Mass Spectrum (m/e): 361 203.
Infrared Absorption Spectrum (liquid) $v_{max}$ cm$^{-1}$:
3300, 1730, 1690, 1600, 1530, 1500, 1460, 1420, 1160.
Nuclear Magnetic Resonance Spectrum (60 MHz, CDCl$_3$) δ ppm:
1.28 (3H, doublet, J=6 Hz);
2.2–2.8 (8H, multiplet);
18 (1H, quartet, J=6 Hz);
3.75 (6H, singlet);
4.2 (1H, singlet);
6.6–7.5 (11H, multiplet);
9.22 (1H, singlet).
Mass Spectrum (m/e): 495, 203.

Compound No. 1-41

Infrared Absorption Spectrum (liquid) $v_{max}$ cm$^{-1}$:
3300, 1690, 1600, 1500, 1220, 1160.
Nuclear Magnetic Resonance Spectrum (60 MHz, CDCl$_3$)
1.39 (3H, doublet, J=6 Mz);
2.28–2.98 (8H, multiplet);
3.33 (1H, quartet, J=6 Hz):
4.3 (1H, singlet);
6.78–8.38 (15H, multiplet):
10.05 (1H, singlet).
Mass Spectrum (m/e): 485, 203.

Compound No. 1-42

Infrared Absorption Spectrum (liquid) $v_{max}$ cm$^{-1}$:
3300, 1680, 1600, 1500, 1330, 1300, 1220.
Nuclear Magnetic Resonance Spectrum (60 MHz, CDCl$_3$) δ ppm:
1.33 (3H, doublet, J=7 Hz);
2.13 (6H, singlet);
2.25 (3H, singlet);
1.88–2.98 (8H, multiplet);
3.18 (1H, quartet, J=7 Hz);
4.26 (1H, singlet);
6.78–7.58 (10H, multiplet);
Mass Spectrum (m/e): 477, 203.

Compound No. 1-48

Infrared Absorption Spectrum (liquid) $v_{max}$ cm$^{-1}$:
3350, 1740, 1670, 1600, 1500, 1450, 1220, 1150.
Nuclear Resonance Spectrum (60 MHz, CDCl$_3$)
1.15 (3H, doublet, J=8 Hz);
1.5–1.8 (6H, multiplet);
1.8–2.2 (9H, multiplet);
2.2–2.7 (8H, multiplet);
2.89 (1H, quartet, J=8 Hz);
4.2 (1H, singlet);
6.8–7.6 (8H, multiplet).
Mass Spectrum (m/e): 493, 315.

Compound No. 1-49

Infrared Absorption Spectrum (liquid) $v_{max}$ cm$^{-1}$:
3300, 1700, 1600.
Nuclear Magnetic Resonance Spectrum (60 MHz, CDCl$_3$)
1.29 (3H, doublet, J=6 Hz);
2.3–2.8 (8H, multiplet);
3.2 (1H, quartet, J=6 Hz);
4.25 (1H, singlet);
6.3–7.5 (11H, multiplet).
Mass Spectrum (m/e): 471, 315, 203.

Compound No. 1-53

Infrared Absorption Spectrum (liquid) $v_{max}$ cm$^{-1}$:
3300, 2950, 1690, 1600, 1530, 1500, 1320, 1220, 1150.
Nuclear Magnetic Resonance Spectrum (60 MHz, CDCl$_3$) δ ppm:
1.3 (3H, doublet, J=7 Hz);
2.2–2.8 (8H, multiplet);
3.34 (1H, quartet, J=7 Hz);
4.2 (1H, singlet);
6.8–7.6 (10H, multiplet).
Mass Spectrum (m/e): 442, 315, 203.

Compound No. 1-54

Infrared Absorption Spectrum (liquid) $v_{max}$ cm$^{-1}$:
3300, 1700, 1600, 1510, 1460, 1220, 1150, 1010.
Nuclear Magnetic Resonance Spectrum (60 MHz, CDCl$_3$) δ ppm:
1.28 (3H, doublet, J=7 Hz):
2.2–3.0 (8H, multiplet):
3.26 (1H, quartet, J=7 Hz);
4.2 (1H, singlet):
6.6–7.6 (11H, multiplet);
8.8 (1H, singlet).
Mass Spectrum (m/e): 471, 203.

Compound No. 1-56

Infrared Absorption Spectrum (liquid) $v_{max}$ cm$^{-1}$:
3475, 1660, 1600, 1500, 1220, 1150, 1010.
Nuclear Magnetic Resonance Spectrum (60 MHz, CDCl$_3$) δ ppm:
2.1–2.7 (8H, multiplet):
2.98 (2H, singlet);
3.23 (3H, singlet);
4.2 (1H, singlet); 6.8–7.7 (12H, multiplet).
Mass Spectrum (m/e): 453, 203.

Compound No. 2-1

Infrared Absorption Spectrum (chloroform) $v_{max}$ cm$^{-1}$: 3300, 2960, 2830, 1685, 1615, 1600, 1520, 1505.
Nuclear Magnetic Resonance Spectrum (60 MHz, CDCl$_3$) δ ppm:
1.7–2.6 (9H, multiplet);
2.1–3.3 (4H, multiplet);
3.2–3.8 (2H, multiplet);
4.3–4.9 (1H, multiplet);
5.12 (1H, singlet);
6.0–6.7 (2H, multiplet);
6.7–7.7 (10H, multiplet);
9.57 (1H, broad singlet).
Mass Spectrum (m/e): 481, 203.

Compound No. 2-2

Infrared Absorption Spectrum (liquid) $v_{max}$ cm$^{-1}$:
3300, 2975, 2925, 2830, 1680, 1605, 1500.

Nuclear Magnetic Resonance Spectrum (60 MHz, CDCl₃) δ ppm:
0.7-1.9 (19H, multiplet);
2.12 (6H, singlet);
2.23 (3H, singlet);
2.0-3.3 (6H, multiplet);
3.3-4.0 (1H, multiplet);
5.15 (1H, singlet);
6.7-7.7 (12H, multiplet);
6.55 (0.5H, broad singlet); 6.87 (0.5H, broad singlet).
Mass Spectrum (m/e): 505, 343, 203.

Compound No. 2-5

Infrared Absorption Spectrum (chloroform) $\nu_{max}$ cm⁻¹: 3300, 2910, 1665, 1605, 1505.
Nuclear Magnetic Resonance Spectrum (60 MHz, CDCl₃) δ ppm:
1.01 (3H, doublet, J=6 Hz);
1.12 (3H, doublet, J=6 Hz);
1.5-1.8 (6H, multiplet);
1.8-2.3 (11H, multiplet);
2.3-3.1 (6H, multiplet);
4.92 (1H, singlet);
6.7-7.6 (8H, multiplet).
Mass Spectrum (m/e): 507, 203.

Compound No. 2-6

Infrared Absorption Spectrum (liquid) $\nu_{max}$ cm⁻¹: 1740, 1640, 1500, 1460, 1220, 1150, 1050.
Nuclear Magnetic Resonance Spectrum (60 MHz, CDCl₃) δ ppm:
0.7-4.6 (30H, multiplet):
4.19 (1H, singlet);
6.8-7.6 (8H, multiplet).
Mass Spectrum (m/e): 495, 203.

Compound No. 2-8

Infrared Absorption Spectrum (liquid) $\nu_{max}$ cm⁻¹: 3305, 2975, 2925, 2825, 1680, 1600, 1500.
Nuclear Magnetic Resonance Spectrum (60 MHz, CDCl₃)
1.18 (6H, doublet, J=6 Hz);
2.12 (6H, singlet);
2.21 (3H, singlet);
2.2-3.4 (8H, multiplet);
5.12 (1H, singlet);
6.7-7.7 (10H, multiplet);
6.67 (1H, broad singlet).
Mass Spectrum (m/e): 491, 203.

Compound No. 2-9

Nuclear Magnetic Resonance Spectrum (60 MHz, CDCl₃) δ ppm:
1.06 (3H, doublet, J=6 Hz);
1.16 (3H, doublet, J=6 Hz);
2.1-3.0 (6H, multiplet);
3.08 (1H, singlet);
3.17 (1H, singlet);
3.78 (3H, singlet);
3.81 (6H, singlet);
5.03 (1H, singlet);
6.86 (2H, singlet);
6.7-7.7 (8H, multiplet);
9.13 (1H, broad singlet).
Mass Spectrum (m/e): 539, 203.

Compound No. 2-10

Infrared Absorption Spectrum (chloroform) $\nu_{max}$ cm⁻¹: 3280, 2950, 2800, 1700, 1625, 1600, 1530, 1500.
Nuclear Magnetic Resonance Spectrum (60 MHz, CDCl₃) δ ppm:
1.05 (3H, doublet, J=6 Hz);
1.15 (3H, doublet, J=6 Hz);
1.7-2.1 (6H, multiplet);
3.08 (1H, AB-type, J=18 Hz);
3.23 (1H, AB-type, J=18 Hz);
4.99 (1H, singlet);
6.4-7.7 (9H, multiplet);
7.9-8.5 (2H, multiplet);
9.70 (1H, broad singlet).
Mass Spectrum (m/e): 485, 203.

Compound No. 2-12

Infrared Absorption Spectrum (liquid) $\nu_{max}$ cm⁻¹: 3300, 1670, 1600, 1500, 1440, 1220, 1140.
Nuclear Magnetic Resonance Spectrum (60 MHz, CDCl₃) δ ppm:
1.08 (3H, doublet, J=6 Hz);
1.8-2.3 (1H, multiplet);
2.4-2.7 (6H, multiplet);
2.95 (1H, doublet, J=18 Hz);
3.45 (1H, doublet, J=18 Hz);
4.22 (1H, singlet);
6.6-7.7 (12H, multiplet);
9.35 (1H, singlet).
Mass Spectrum (m/e): 453, 203.

Compound No. 2-13

Infrared Absorption Spectrum (liquid) $\nu_{max}$ cm⁻¹: 3300, 1680, 1600, 1500, 1450, 1410, 1220, 1130, 1020.
Nuclear Magnetic Resonance Spectrum (60 MHz, CDCl₃) δ ppm:
1.0 (3H, doublet, J=6 Hz);
1.76-3.0 (7H, multiplet);
2.9 (1H, doublet, J=16 Hz);
3.4 (1H, doublet, J=16 Hz);
3.77 (3H, singlet);
3.84 (6H, singlet;
4.21 (1H, singlet);
6.8-7.56 (10H, multiplet);
9.1 (1H, singlet).
Mass Spectrum (m/e): 525, 203.

Compound No. 2-14

Infrared Absorption Spectrum (liquid) $\nu_{max}$ cm⁻¹: 3300, 1690, 1620, 1610, 1450, 1320, 1220, 1150, 1100.
Nuclear Magnetic Resonance Spectrum (60 MHz, CDCl₃) δ ppm:
1.01 (3H, doublet, J=6 Hz);
1.73-2.98 (7H, multiplet);
2.93 (1H, doublet, J=17 Hz);
3.48 (1H, doublet, J=17 Hz);
4.22 (1H, singlet);
6.78-7.58 (11H, multiplet);
8.23-8.68 (1H, multiplet);
9.76 (1H, singlet).
Mass Spectrum (m/e): 453, 203.

Compound No. 2-15

Infrared Absorption Spectrum (liquid) $\nu_{max}$ cm⁻¹: 3300, 1690, 1600, 1500, 1400, 1300, 1220, 1050.
Nuclear Magnetic Resonance Spectrum (60 MHz, CDCl₃) δ ppm:

0.98 (3H, doublet, J=6 Hz);
1.6-3.2 (7H, multiplet);
2.9 (1H, doublet, J=16 Hz);
3.45 (1H, doublet, J=16 Hz);
4.21 (1H, singlet);
6.7-7.8 (12H, multiplet);
9.22 (1H, multiplet).
Mass Spectrum (m/e): 453, 203.

Compound No. 2-16

Infrared Absorption Spectrum (liquid) $\nu_{max}$ cm$^{-1}$: 3310, 2980, 2840, 1700, 1620, 1600, 1530.
Nuclear Magnetic Resonance Spectrum (60 MHz, CDCl$_3$) δ ppm:
  1.05 (3H, doublet, J=6 Hz);
  1.16 (3H, doublet, J=6 Hz);
  2.1-3.0 (6H, multiplet);
  3.12 (1H, singlet);
  3.19 (1H, multiplet);
  4.98 (1H, multiplet);
  6.7-7.7 (11H, multiplet);
  8.1-8.7 (1H, multiplet);
  9.60 (1H, broad singlet).
Mass Spectrum (m/e): 467, 203.

Compound No. 2-17

Infrared Absorption Spectrum (KBr) $\nu_{max}$ cm$^{-1}$: 3425, 3250, 2990, 2840, 1695, 1605, 1540, 1505.
Nuclear Magnetic Resonance Spectrum (60 MHz, CDCl$_3$) δ ppm:
  1.04 (3H, doublet, J=6 Hz);
  1.28 (3H doublet, J=6 Hz):
  1.7-3.0 (6H, multiplet):
  3.05 (1H, AB-type, J=16 Hz):
  3.40 (1H, AB-type, J=16 Hz):
  5.20 (1H, singlet);
  7.7-8.0 (14H, multiplet);
  8.29 (1H, doublet of doublets, J=2.6 Hz);
  10.06 (1H, broad singlet).
Mass Spectrum (m/e): 499, 203.

Compound No. 2-21

Infrared Absorption Spectrum (liquid) $\nu_{max}$ cm$^{-1}$: 3300, 2990, 2840, 1735, 1690, 1600, 1515.
Nuclear Magnetic Resonance Spectrum (60 MHz, CDCl$_3$) δ ppm:
  1.15 (3H, doublet, J=6 Hz);
  1.16 (3H, doublet, J=6 Hz);
  2.1-3.1 (6H, multiplet);
  3.10 (1H, singlet);
  3.20 (1H, singlet);
  5.03 (1H, singlet);
  6.5-7.7 (12H, multiplet);
  9.31 (1H, broad singlet).
Mass Spectrum (m/e); 467, 203.

Compound No. 2-22

Infrared Absorption Spectrum (chloroform) $\nu_{max}$ cm$^{-1}$: 3290, 2950, 2810, 1680, 1605, 1505.
Nuclear Magnetic Resonance Spectrum (60 MHz, CDCl$_3$) δ ppm:
  1.05 (3H, doublet, J=6 Hz);
  1.19 (3H, doublet, J=6 Hz);
  1.7-3.3 (8H, multiplet);
  5.04 (1H, singlet);
  6.6-7.8 (12H, multiplet);
  9.17 (1H, broad singlet).
Mass Spectrum (m/e): 467, 203.

Compound No. 2-23

Infrared Absorption Spectrum (chloroform) $\nu_{max}$ cm$^{-1}$: 3300, 2975, 2830, 1675, 1605, 1510.
Nuclear Magnetic Resonance Spectrum (60 MHz, CDCl$_3$) δ ppm:
  0.7-1.5 (9H, multiplet);
  1.76 (2H, sextet, J=7 Hz);
  2.2-3.1 (6H, multiplet);
  3.07 (1H, singlet);
  3.18 (1H, singlet):
  3.88 (2H, triplet, J=7 Hz);
  5.06 (1H, singlet);
  6.7-7.8 (12H, multiplet);
  9.08 (1H, broad singlet).
Mass Spectrum (m/e): 507, 203.

Compound No. 2-24

Infrared Absorption Spectrum (liquid) $\nu_{max}$ cm$^{-1}$: 3375, 2990, 2840, 1745, 1680, 1600, 1505.
Nuclear Magnetic Resonance Spectrum (60 MHz, CDCl$_3$) δ ppm:
  0.8-1.5 (9H, multiplet);
  1.6-2.9 (6H, multiplet);
  2.98 (1H, singlet);
  3.12 (1H, singlet);
  3.8-4.4 (4H, multiplet);
  5.08 (1H, singlet);
  6.7-7.9 (8H, multiplet).
Mass Spectrum (m/e): 459, 203.

Compound No. 2-62

Infrared Absorption Spectrum (liquid) $\nu_{max}$ cm$^{-1}$: 3275, 1730, 1660, 1600, 1500, 1380, 1220, 1140.
Nuclear Magnetic Resonance Spectrum (60 MHz, CDCl$_3$) δ ppm:
  1.21 (1.5H, doublet, J=7 Hz);
  1.32 (1.5H, doublet, J=7 Hz);
  1.55 (3H, doublet, J=7 Hz);
  2.09 (6H, singlet);
  2.21 (3H, singlet);
  1.7-3.2 (7H, multiplet);
  3.38 (1H, quartet, J=7 Hz);
  4.15 (1H, singlet);
  5.32 (1H, quartet, J=7 Hz);
  6.7-7.5 (10H, multiplet);
  8.8 (1H, singlet).
Mass Spectrum (m/e): 491.

Compound No. 2-63

Infrared Absorption Spectrum (liquid) $\nu_{max}$ cm$^{-1}$: 3300, 1690, 1600, 1510, 1380, 1300, 1220.
Nuclear Magnetic Resonance Spectrum (60 MHz, CDCl$_3$) δ ppm:
  1.0-1.7 (6H, multiplet):
  3.45 (1H, quartet, J=6 Hz);
  4.2 (1H, singlet);
  6.7-7.6 (11H, multiplet);
  9.1 (1H, singlet).
Mass Spectrum (m/e): 485, 203.

Compound No. 2-64

Infrared Absorption Spectrum (liquid) $\nu_{max}$ cm$^{-1}$: 3300, 1740, 1700, 1600, 1530, 1500, 1220, 1160, 1100.
Nuclear Magnetic Resonance Spectrum (60 MHz, CDCl$_3$) δ ppm:
  0.9-1.5 (6H, multiplet);
  1.7-3.1 (7H, multiplet);

3.8 (1H, quartet, J=7 Hz);
4.22 (1H, singlet);
6.7-8.3 (15H, multiplet);
10.04 (1H, singlet).
Mass Spectrum (m/e): 499, 329.
Infrared Absorption Spectrum (chloroform) $\nu_{max}$ cm$^{-1}$:
3430, 3000, 2920, 2860, 1670, 1635, 1540.
Nuclear Magnetic Resonance Spectrum (60 MHz, CDCl$_3$) δ ppm:
1.35 (3H, doublet, J=7 Hz);
1.5-1.8 (6H, multiplet);
1.8-2.3 (9H, multiplet);
2.3-3.8 (5H, multiplet);
3.92 (2H, singlet);
4.86 (1H, singlet);
19 (1H, singlet);
6.7-7.7 (8H, multiplet).
Mass Spectrum (m/e): 507, 203.

Compound No. 3-2

Infrared Absorption Spectrum (KBr) $\nu_{max}$ cm$^{-1}$:
3225, 2910, 1665, 1600, 1500.
Nuclear Magnetic Resonance Spectrum (60 MHz, CDCl$_3$) δ ppm:
2.16 (3H, singlet);
2.23 (6H, singlet);
2.68 (2H, triplet, J=6 Hz);
3.12 (2H, singlet);
3.53 (2H, triplet, J=6 Hz);
4.16 (2H, singlet);
4.31 (1H, singlet);
6.7-7.6 (8H, multiplet);
7.00 (2H, singlet);
7.85 (1H, broad singlet).
Mass Spectrum (m/e): 477, 203.

Compound No. 3-9

Nuclear Magnetic Resonance Spectrum (60 MHz, CDCl$_3$) δ ppm:
1.43 (3H, doublet, J=7 Hz);
2.12 (6H, singlet);

2.23 (3H, singlet);
2.4-2.9 (2H, multiplet);
3.08 (1H, singlet);
3.20 (1H, singlet);
3.2-3.7 (2H, multiplet);
4.27 (1H, singlet);
5.33 (1H, quartet, J=7 Hz);
6.7-7.6 (10H, multiplet);
7.72 (1H, broad singlet).
Mass Spectrum (m/e): 491, 203.

Compound No. 3-10

Infrared Absorption Spectrum (liquid) $\nu_{max}$ cm$^{-1}$:
3300 1740, 1680, 1640, 1500, 1450, 1220, 1010.
Nuclear Magnetic Resonance Spectrum (60 MHz, CDCl$_3$) δ ppm:
1.31 (3H, doublet, J=7 Hz);
1.5-3.6 (22H, multiplet);
4.26 (1H, singlet);
5.05 (1H, quartet, J=7 Hz);
6.00 (1H, singlet);
6.8-7.6 (8H, multiplet).
Mass Spectrum (m/e): 507, 203.

Compound No. 3-11

Infrared Absorption Spectrum (liquid) $\nu_{max}$ cm$^{-1}$:
3300, 1690, 1620, 1540, 1500, 1220, 1010.
Nuclear Magnetic Resonance Spectrum (60 MHz, CDCl$_3$) δ ppm:
1.42 (3H, doublet, J=7 Hz);
2.3-3.6 (7H, multiplet);
4.07 (1H, quartet, J=7 Hz);
5.22 (1H, singlet);
6.6-7.7 (12H, multiplet);
8.91 (1H, singlet).
Mass Spectrum (m/e); 467, 203.

Compound No. 5-8

Infrared Absorption Spectrum (liquid) $\nu_{max}$ cm$^{-1}$:
3450.
Nuclear Magnetic Resonance Spectrum (60 MHz, CDCl$_3$) δ ppm:
2.25-2.6 (4H, multiplet);
2.4-2.8 (4H, multiplet);
2.9-3.3 (4H, multiplet);
4.21 (1H, singlet);
6.4-7.5 (12H, multiplet).
Mass Spectrum (m/e): 425, 203.

Compound No. 5-10

Infrared Absorption Spectrum (liquid) $\nu_{max}$ cm$^{-1}$:
3455.
Nuclear Magnetic Resonance Spectrum (60 MHz, CDCl$_3$) δ ppm:
1.0 (3H, doublet, J=6 Hz);
1.1 (3H, doublet, J=6 Hz);
1.7-3.2 (8H, multiplet);
3.68 (3H, singlet); 3.95 (2H, multiplet); 4.95 (1H, singlet); 6.5-7.5 (12H, multiplet).
Mass Spectrum (m/e): 464.

Compound No. 5-11

Infrared Absorption Spectrum (liquid) $\nu_{max}$ cm$^{-1}$:
3450.
Nuclear Magnetic Resonance Spectrum (60 MHz, CDCl$_3$) δ ppm:
2.25-2.6 (4H, multiplet);
2.55-2.9 (4H, multiplet);
3.05-3.4 (4H, multiplet);
4.15 (1H, singlet);
6.4-8.0 (15H, multiplet).
Mass Spectrum (m/e): 457, 203.

Compound No. 7-1

Infrared Absorption Spectrum (liquid) $\nu_{max}$ cm$^{-1}$:
3450. 1640. 1600, 1500, 1440, 1340, 1220. 1150.
Nuclear Magnetic Resonance Spectrum (60 MHz, CDCl$_3$) δ ppm:
1.4-2.1 (6H, multiplet);
2.3-3.0 (8H, multiplet);
3.3 (2H, singlet);
3.2-3.7 (6H, multiplet);
4.6 (1H, singlet);
6.7-7.6 (8H, multiplet).
Mass Spectrum (m/e): 413, 203.
Infrared Absorption Spectrum (liquid) $\nu_{max}$ cm$^{-1}$:
1650, 1600, 1500, 1390, 1220, 1150.
Nuclear Magnetic Resonance Spectrum (60 MHz, CDCl$_3$) δ ppm:
1.4-2.2 (4H, multiplet);
2.3-3.1 (10H, multiplet);

3.5 (2H, singlet);
3.8 (2H, triplet, J=7 Hz);
4.58 (1H, singlet);
6.7-7.7 (12H, multiplet).
Mass Spectrum (m/e): 475, 203.
Infrared Absorption Spectrum (liquid) $\nu_{max}$ cm$^{-1}$:
1740, 1640, 1500, 1410, 1220, 1150.
Nuclear Magnetic Resonance Spectrum (60 MHz, CDCl$_3$)
0.6-4.7 (30H, multiplet);
4.6 (1H, singlet);
6.7-7.6 (8H, multiplet).
Infrared Absorption Spectrum (m/e): 495, 203.

Compound No. 7-5

Infrared Absorption Spectrum (liquid) $\nu_{max}$ cm$^{-1}$:
3300, 1680, 1600, 1510, 1410, 1300, 1220.
Nuclear Magnetic Resonance Spectrum (60 MHz, CDCl$_3$) δ ppm:
1.5-2.1 (2H, multiplet): 2.4-3.1 (8H, multiplet); 3.25 (2H, singlet); 3.76 (3H, singlet); 4.61 (1H, singlet); 6.8-7.7 (12H, multiplet); 9.2 (1H, singlet).
Mass Spectrum (m/e): 465, 203.

Compound No. 7-6

Nuclear Magnetic Resonance Spectrum (60 MHz, CDCl$_3$) δ ppm:
0.93 (6H, doublet, J=6 Hz);
1.5-2.1 (3H, multiplet);
2.4-3.3 (10H, multiplet);
3.18 (2H, singlet);
4.6 (1H, singlet);
6.8-7.6 (8H, multiplet).
Mass Spectrum (m/e): 415, 203.

Compound No. 7-7

Infrared Absorption Spectrum (liquid) $\nu_{max}$ cm$^{-1}$:
3300, 1680, 1600, 1500, 1450, 1420, 1340, 1220, 1140.
Nuclear Magnetic Resonance Spectrum (60 MHz, CDCl$_3$) δ ppm:
1.45-2.25 (2H, multiplet):
2.45-3.05 (8H, multiplet):
3.25 (2H, singlet);
3.8 (3H, singlet);
3.82 (6H, singlet);
4.6 (1H, singlet);
6.8-7.55 (10H, multiplet);
9.21 (1H, singlet).
Mass Spectrum (m/e); 525, 203.

Compound No. 7-8

Infrared Absorption Spectrum (liquid) $\nu_{max}$ cm$^{-1}$:
3400, 1740, 1670, 1600, 1510, 1450, 1220, 1160.
Nuclear Magnetic Resonance Spectrum (60 MHz, CDCl$_3$) δ ppm:
1.3-2.0 (2H, multiplet);
2.3-3.0 (8H, multiplet);
3.2 (2H, singlet);
4.41 (1H, singlet):
4.52 (2H, singlet);
6.8-7.5 (8H, multiplet);
7 3 (5H, singlet).
Mass Spectrum (m/e); 449, 315, 245.

Compound No. 7-10

Infrared Absorption Spectrum (liquid) $\nu_{max}$ cm$^{-1}$:
3350, 1670, 1600, 1500, 1220. 1150.
Nuclear Magnetic Resonance Spectrum (60 MHz, CDCl$_3$) δ ppm:
0.7-2.1 (13H, multiplet);
2.3-3.0 (8H, multiplet);
3.1 (2H, singlet);
4.6 (1H, singlet);
6.8-7.6 (8H, multiplet).
Mass Spectrum (m/e): 441, 203.

Compound No. 7-11

Infrared Absorption Spectrum (liquid) $\nu_{max}$ cm$^{-1}$:
3300, 1740, 1680, 1600, 1500, 1370, 1220.
Nuclear Magnetic Resonance Spectrum (60 MHz, CDCl$_3$) δ ppm:
1.5-2.1 (2H, multiplet);
2.18 (6H, singlet);
2.25 (3H, singlet):
2.5-3.1 (8H, multiplet):
3.32 (2H, singlet):
4.58 (1H, singlet);
6.8-7.5 (10H, multiplet);
8.7 (1H, singlet).
Mass Spectrum (m/e): 477, 203.

Compound No. 7-12

Infrared Absorption Spectrum (liquid) $\nu_{max}$ cm$^{-1}$:
3350, 1680, 1600, 1500, 1220, 1150.
Nuclear Magnetic Resonance Spectrum (60 MHz, CDCl$_3$) δ ppm:
1.73 (6H, singlet);
1.46-2.06 (2H, multiplet);
2.46-3.06 (8H, multiplet);
3.1 (2H, singlet);
4.56 (1H, singlet);
6.76-7.56 (13H, multiplet);
7.76 (1H, singlet).
Mass Spectrum (m/e): 477, 203.

Compound No. 7-13

Infrared Absorption Spectrum (liquid) $\nu_{max}$ cm$^{-1}$:
3300, 1690, 1600, 1500, 1440, 1220, 1150.
Nuclear Magnetic Resonance Spectrum (60 MHz, CDCl$_3$) δ ppm:
1.58-2.28 (2H, multiplet);
2.48-3.18 (8H, multiplet);
3.34 (2H, singlet);
4.63 (1H, singlet);
6.58-7.78 (12H, multiplet);
9.53 (1H, singlet).
Mass Spectrum (m/e): 453, 203.

Compound No. 7-14

Infrared Absorption Spectrum (liquid) $\nu_{max}$ cm$^{-1}$:
3300, 1700, 1620, 1600, 1450, 1320, 1220, 1150, 1100.
Nuclear Magnetic Resonance Spectrum (60 MHz, CDCl$_3$) δ ppm:
1.45-2.05 (2H, multiplet);
2.5-3.1 (8H, multiplet);
3.25 (2H singlet);
4.56 (1H, singlet);
6.76-7.55 (11H, multiplet);
8.25-8.65 (1H, multiplet);
9.7 (1H, singlet).
Mass Spectrum (m/e): 453, 250, 203.

Compound No. 7-15

Infrared Absorption Spectrum (liquid) $\nu_{max}$ cm$^{-1}$:
3450, 3300, 1680, 1600, 1510, 1420, 1220.

Nuclear Magnetic Resonance Spectrum (60 MHz, CDCl$_3$) δ ppm:
 1.0 (3H, triplet, J=6 Hz);
 1.4-2.2 (4H, multiplet);
 2.4-3.1 (8H, multiplet);
 3.22 (2H, singlet);
 3.88 (2H, triplet, J=6 Hz);
 4.6 (1H, singlet);
 6.79-7.7 (10H, multiplet);
 9.18 (1H, singlet);

Compound No. 7-16

Infrared Absorption Spectrum (liquid) $v_{max}$ cm$^{-1}$: 350, 1740, 1670, 1600, 1500, 1370, 1220.
Nuclear Magnetic Resonance Spectrum (60 MHz, CDCl$_3$) δ ppm:
 1.22 (3H, triplet, J=7 Hz);
 1.4-2.0 (2H, multiplet);
 2.3-3.0 (8H, multiplet);
 3.14 (2H, singlet);
 4.01 (2H, doublet, J=5 Hz):
 4.16 (2H, quartet, J=7 Hz);
 4.55 (1H, singlet);
 6.7-7.5 (8H, multiplet);
 7.71 (1H, triplet, J=5 Hz).
Mass Spectrum (m/e): 445, 203.

Compound No. 7-17

Infrared Absorption Spectrum (liquid) $v_{max}$ cm$^{-1}$: 3300, 1670, 1600, 1500, 1220, 1150.
Nuclear Magnetic Resonance Spectrum (60 MHz, CDCl$_3$) δ ppm:
 1.4-2.2 (17H, multiplet);
 2.4-3.0 (8H, multiplet);
 3.0 (2H, singlet);
 4.6 (1H, singlet);
 6.8-7.6 (8H, multiplet).
Mass Spectrum (m/e): 493, 290, 315.

Compound No. 7-18

Infrared Absorption Spectrum (liquid) $v_{max}$ cm$^{-1}$: 3300, 1680, 1600, 1500, 1340, 1220, 1040.
Nuclear Magnetic Resonance Spectrum (60 MHz, CDCl$_3$) δ ppm:
 1.5-2.2 (2H, multiplet);
 2.3-3.1 (8H, multiplet);
 3.22 (2H, singlet);
 4.6 (1H, singlet);
 5.88 (2H, singlet);
 6.6-7.6 (11H, multiplet);
 9.18 (1H, singlet).
Mass Spectrum (m/e): 479, 203.

Compound No. 7-26

Infrared Absorption Spectrum (liquid) $v_{max}$ cm$^{-1}$: 3300, 1700, 1600, 1150, 1010.
Nuclear Magnetic Resonance Spectrum (60 MHz, CDCl$_3$) δ ppm:
 1.5-2.1 (2H, mutltiplet);
 2.4-3.1 (8H, multiplet); 3.31 (2H, singlet); 4.59 (1H, singlet); 6.7-7.7 (11H, multiplet); 8.91 (1H, singlet).
Mass Spectrum (m/e): 471.

Compound No. 7-30

Infrared Absorption Spectrum (liquid) $v_{max}$ cm$^{-1}$: 3400, 1670, 1600, 1510, 1460, 1300, 1220.
Nuclear Magnetic Resonance Spectrum (60 MHz, CDCl$_3$) δ ppm:
 1.4-1.9 (2H, multiplet);
 2.2-2.9 (8H, multiplet):
 3.15 (2H, singlet);
 3.75 (3H, singlet);
 4.35 (1H, singlet);
 4.5 (2H, doublet, J=5 Hz);
 6.75-7.85 (13H, multiplet).
Mass Spectrum (m/e): 479, 315, 276.

Compound No. 7-38

Infrared Absorption Spectrum (liquid) $v_{max}$ cm$^{-1}$: 1650, 1600, 1500, 1220, 830.
Nuclear Magnetic Resonanoe Spectrum (60 MHz, CDCl$_3$) δ ppm:
 1.18 (3H, doublet, J=6 Hz):
 1.2-2.2 (4H, multiplet):
 2.4-3.0 (10H, multiplet):
 3.3-4.2 (3H, multiplet);
 4.52 (1H, singlet);
 6.7-7.9 (12H, multiplet).
Mass Spectrum (m/e): 489, 203.
Infrared Absorption Spectrum (liquid) $v_{max}$ cm$^{-1}$: 3300, 1680, 1600, 1500, 1450, 1420, 1220, 1150.
Nuclear Magnetic Resonance Spectrum (60 MHz, CDCl$_3$) δ ppm:
 1.3 (3H, doublet, J=6 Hz);
 1.4-2.0 (2H, multiplet);
 2.3-3.0 (8H, multiplet):
 3.4 (1H, quartet, J=6 HZ);
 3.78 (6H, singlet);
 4.61 (1H, singlet);
 6.8-7.61 (1H, multiplet);
 9.48 (1H, singlet).
Mass Spectrum (m/e): 509, 203.

Compound No. 7-44

Infrared Absorption Spectrum (liquid) $v_{max}$ cm$^{-1}$: 3325, 1690, 1600, 1530, 1500, 1220, 920.
Nuclear Magnetic Resonance Spectrum (60 MHz, CDCl$_3$)
 1.34 (3H, doublet, J=6 Hz);
 1.5-2.2 (2H, multiplet);
 2.5-3.2 (8H, multiplet);
 3.55 (1H, quartet, J=6 HZ);
 4.55 (1H, singlet);
 6.7-8.4 (15H, multiplet);
 0.15 (1H, singlet).
Mass Spectrum (m/e): 543, 203.

Compound No. 7-45

Infrared Absorption Spectrum (liquid) $v_{max}$ cm$^{-1}$: 3350, 1680, 1600, 1500, 1380, 1220, 1160.
Nuclear Magnetic Resonance Spectrum (60 MHz, CDCl$_3$) δ ppm:
 1.31 (3H, triplet, J=6 Hz);
 1.4-2.0 (2H, multiplet);
 2.4-3.1 (8H, multiplet);
 3.41 (1H, quartet, J=6 Hz);
 4.54 (1H, singlet);
 6.7-7.5 (10H, multiplet);
 8.7 (1H, singlet).
Mass Spectrum (m/e): 491, 203.

Compound No. 7-57

Infrared Absorption Spectrum (liquid) $v_{max}$ cm$^{-1}$: 3300, 1730, 1680, 1600, 1410, 1320.
Nuclear Magnetic Resonance Spectrum (60 MHz, CDCl$_3$) δ ppm:

1.32 (3H, doublet, J=6 Hz);
1.5-2.1 (2H, multiplet);
2.5-3.0 (8H, multiplet);
3.52 (1H, quartet, J=6 Hz);
4.59 (1H, singlet);
6.8-7.7 (10H, multiplet).
Mass Spectrum (m/e): 456, 203.

Compound No. 7-58

Infrared Absorption Spectrum (liquid) $\nu_{max}$ cm$^{-1}$: 3325, 1700, 1600, 1510, 1220, 1160, 1020.

Nuclear Magnetic Resonance Spectrum (60 MHz, CDCl$_3$)
1.28 (3H, doublet, J=7 Hz);
1.5-2.1 (2H, multiplet);
2.4-3.1 (8H, multiplet);
3.5 (1H, quartet, J=7 Hz);
4.6 (1H, singlet);
6.7-7.6 (11H, multiplet)
9.0 (1H, singlet).
Mass Spectrum (m/e): 485, 203.

Compound No. 1-69

Infrared Absorption Spectrum (liquid) $\nu_{max}$ cm$^{-1}$: 3310, 2940, 2800, 1685, 1595, 1515, 1495.

Nuclear Magnetic Resonance Spectrum (60 MHz, CDCl$_3$)
2.1-2.8 (8H, multiplet);
3.07 (2H, singlet);
3.71 (6H, singlet);
4.22 (1H, singlet);
6.6-7.7 (13H, multiplet);
9.00 (1H, broad singlet).
Mass Spectrum (m/e): 449, 201.

Infrared Absorption Spectrum (chloroform) $\nu_{max}$ cm$^{-1}$: 3300, 3000, 2840, 1690, 1618, 1525, 1497.

Nuclear Magnetic Resonance Spectrum (60 MHz, CDC$_3$) δ ppm:
2.1-2.9 (8H, multiplet);
3.07 (2H, singlet);
4.21 (1H singlet);
9.24 (1H, broad singlet).
Mass Spectrum (m/e): 437, 201.

We claim:

1. A compound of the formula (I-2)

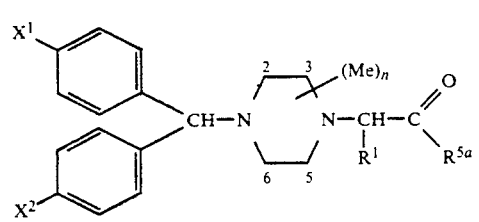

(I-2)

wherein
Me is methyl,
$X^1$ is hydrogen, chlorine or fluorine,
$X^2$ is hydrogen, chlorine or fluorine,
$R^1$ is hydrogen or $C_1$-$C_6$ alkyl,
$R^{5a}$ is 2,4,6-trimethylphenyl-NH,
1,1-dimethylbenzyl-NH, 3-fluorophenyl-NH,
3-fluorophenyl-N-allyl, and 4-methoxyphenyl-NH; and
n is 0-3.

2. A compound as claimed in claim 1, wherein $R^1$ represents a hydrogen atom or a $C_1$-$C_4$ alkyl group.

3. A compound as claimed in claim 1, wherein $R^1$ represents a hydrogen atom or a $C_1$-$C_2$ alkyl group.

4. A compound as claimed in claim 1, wherein $R^1$ represents a hydrogen atom or a methyl group.

5. A compound as claimed in claim 1, wherein both of $X^1$ and $X^2$ represent fluorine atoms.

6. A compound as claimed in claim 1, wherein one of $X^1$ and $X^2$ represents a chlorine atom and the other represents a hydrogen atom.

7. A compound as claimed in claim 1, selected from the group consisting of 1-[bis(4-fluorophenyl)methyl]-4-(2,4,6-trimethylphenylcarbamoylmethyl)piperazine and pharmaceutically acceptable salts thereof.

8. A compound as claimed in claim 1, selected from the group consisting of 1-[bis(4-fluorophenyl)methyl]-4-(1,1-dimethylbenzylcarbamoylmethyl)piperazine and pharmaceutically acceptable salts thereof.

9. A compound as claimed in claim 1, selected from the group consisting of 1-[bis(4-fluorophenyl)methyl]-4-(3-fluorophenylcarbamoylmethyl)piperazine and pharmaceutically acceptable salts thereof.

10. A compound as claimed in claim 1, selected from the group consisting of 1-[bis(4-fluorophenyl)methyl]-4-[N-allyl-N-(3-fluorophenyl)carbamoylmethyl]piperazine and pharmaceutically acceptable salts thereof.

11. A compound as claimed in claim 1, selected from the group consisting of 1-(4-chlorobenzhydryl)-4-(4-methoxyphenylcarbamoylmethyl)piperazine and pharmaceutically acceptable salts thereof.

12. A compound as claimed in claim 1, selected from the group consisting of 1-(4-chlorobenzhydryl)-4-(2,4,6-trimethylphenylcarbamoylmethyl)piperazine and pharmaceutically acceptable salts thereof.

13. A compound as claimed in claim 1, selected from the group consisting of 1-[bis(4-fluorophenyl)methyl]-4-[(4-methoxyphenyl)carbamoylmethyl]-2,5-dimethylpiperazine and pharmaceutically acceptable salts thereof.

14. A compound as claimed in claim 1, selected from the group consisting of 1-[bis(4-fluorophenyl)methyl]-4-[(2,4,6-trimethylphenyl)carbamoylmethyl]-3-methylpiperazine and pharmaceutically acceptable salts thereof.

15. A compound as claimed in claim 1, selected from the group consisting of 1-[bis(4-fluorophenyl)methyl]-4-[(3-fluorophenyl)carbamoylmethyl]-3,3-dimethylpiperazine and pharmaceutically acceptable salts thereof.

16. A pharmaceutical composition comprising an effective amount of a calcium-entry blocker in admixture with a pharmaceutically acceptable carrier or diluent, wherein said calcium-entry blocker is a compound of claim 1.

17. A composition as claimed in claim 16, in which said calcium-entry blocker is selected from the group consisting of:
1-[bis(4-fluorophenyl)methyl]-4-(2,4,6-trimethylphenylcarbamoylmethyl)piperazine;
1-[bis(4-flurophenyl)methyl]-4-(1,1-dimethylbenzylcarbamoylmethyl)piperazine;
1-[bis(4-fluorophenyl)methyl]-4-(3-fluorophenylcarbamoylmethyl)piperazine;
1-[bis(4-fluorophenyl)methyl]-4-[N-allyl-N-(3-fluorophenyl)carbamoylmethyl]piperazine;
1-[bis(4-fluorophenyl)methyl]-4-[1-(3-fluorophenylcarbamoyl)ethyl]piperazine;
1-(4-chlorobenzhydryl)-4-(4-methoxyphenylcarbamoylmethyl)piperazine;
1-(4-chlorobenzhydryl)-4-(2,4,6-trimethylphenylcarbamoylmethyl)piperazine;

1-[bis(4-fluorophenyl)methyl]-4-[(4-methoxyphenyl)-carbamoylmethyl]-2,5-dimethylpiperazine;
1-[bis(4-fluorophenyl)methyl]-4-[(2,4,6-trimethylphenyl)carbamoylmethyl]-3-methylpiperazine;
and pharmaceutically acceptable salts thereof.

18. A method for the treatment of vascular disorders in an animal by administering to said animal an effective amount of a calcium-entry blocker, wherein said calcium-entry blocker is a compound as claimed in claim 1.

19. A method as claimed in claim 18, in which said calcium-entry blocker is selected from the group consisting of:
1-[bis(4-fluorophenyl)methyl]-4-(2,4,6-trimethylphenylcarbamoylmethyl)piperazine;
1-[bis(4-fluorophenyl)methyl]-4-(1,1-dimethylbenzylcarbamoylmethyl)piperazine;
1-[bis(4-fluorophenyl)methyl]-4-(3-fluorophenylcarbamoylmethyl)piperazine;
1-[bis(4-fluorophenyl)methyl]-4-[N-allyl-N-(3-fluorophenyl)carbamoylmethyl]piperazine;
1-[bis(4-fluorophenyl)methyl]-4-[1-(3-fluorophenylcarbamoyl)ethyl]piperazine;
1-(4-chlorobenzhydryl)-4-(4-methoxyphenylcarbamoylmethyl)piperazine;
1-(4-chlorobenzhydryl)-4-(2,4,6-trimethylphenylcarbamoylmethyl)piperazine;
1-[bis(4-fluorophenyl)methyl]-4-[(4-methoxyphenyl)-carbamoylmethyl]-2,5-dimethylpiperazine;
1-[bis(4-fluorophenyl)methyl]-4-[(2,4,6-trimethylphenyl)carbamoylmethyl]-3-methylpiperazine;
and pharmaceutically acceptable salts thereof.

20. A method for the treatment of ischemic disorders in an animal by administering to said animal an effective amount of a calcium-entry blocker, wherein said calcium-entry blocker is a compound as claimed in claim 1.

21. A method as claimed in claim 20, in which said calcium-entry blocker is selected from the group consisting of:
1-[bis(4-fluorophenyl)methyl]-4-(2,4,6-trimethylphenylcarbamoylmethyl)piperazine;
1-[bis(4-fluorophenyl)methyl]-4-(1,1-dimethylbenzylcarbamoylmethyl)piperazine;
1-[bis(4-fluorophenyl)methyl]-4-(3-fluorophenylcarbamoylmethyl)piperazine;
1-[bis(4-fluorophenyl)methyl]-4-[N-allyl-N-(3-fluorophenyl)carbamoylmethyl]piperazine:
1-[bis(4-fluorophenyl)methyl]-4-[1-(3-fluorophenylcarbamoyl)ethyl]piperazine;
1-(4-chlorobenzhydryl)-4-(4-methoxyphenylcarbamoylmethyl)piperazine;
1-(4-chlorobenzhydryl)-4-(2,4,6-trimethylphenylcarbamoylmethyl)piperazine;
1-[bis(4-fluorophenyl)methyl]-4-[(4-methoxyphenyl)carbamoylmethy]-2,5-dimethylpiperazine;
1-[bis(4-fluorophenyl)methyl]-4-[(2,4,6-trimethylphenyl)carbamoylmethyl]-3-methylpiperazine;
and pharmaceutically acceptable salts thereof.

22. A method of protecting an animal against the deleterious effects of anoxia by administering to said animal an effective amount of a calcium-entry blocker, wherein said calcium- entry blocker is a compound as claimed in claim 1.

23. A method as claimed in claim 22, in which said calcium-entry blocker is selected from the group consisting of:
1-[bis(4-fluorophenyl)methyl]-4-(2,4,6-trimethylphenylcarbamoylmethyl)piperazine;
1-[bis(4-fluorophenyl)methyl]-4-(1,1-dimethylbenzylcarbamoylmethyl)piperazine;
1-[bis(4-fluorophenyl)methyl]-4-(3-fluorophenylcarbamoylmethyl)piperazine;
1-[bis(4-fluorophenyl)methyl]-4-[N-allyl-N-(3-fluorophenyl)carbamoylmethyl]piperazine;
1-[bis(4-fluorophenyl)methyl]-4-[1-(3-fluorophenylcarbamoyl)ethyl]piperazine;
1-(4-chlorobenzhydryl)-4-(4-methoxyphenylcarbamoylmethyl)piperazine;
1-(4-chlorobenzhydry (2,4,6-trimethylphenylcarbamoylmethyl)piperazine;
1-[bis(4-fluorophenyl)methyl]-4-[(4-methoxyphenyl)-carbamoylmethyl]-2,5-dimethylpiperazine;
1-[bis(4-fluorophenyl)methyl]-4-[(2,4,6-trimethylphenyl)carbamoylmethyl]-3-methylpiperazine;
and pharmaceutically acceptable salts thereof.

* * * * *